United States Patent [19]

Deleys et al.

[11] Patent Number: 5,922,532
[45] Date of Patent: Jul. 13, 1999

[54] SYNTHETIC ANTIGENS FOR THE DETECTION OF ANTIBODIES TO HEPATITIS C VIRUS

[75] Inventors: Robert J. Deleys, Grimbergen; Dirk Pollet, Wijnegem; Geert Maertens, Brugge; Hugo Van Heuverswijn, Laarne, all of Belgium

[73] Assignee: Innogenetics, N.V., Ghent, Belgium

[21] Appl. No.: 08/391,671

[22] Filed: Feb. 21, 1995

Related U.S. Application Data

[63] Continuation of application No. 07/920,286, filed as application No. PCT/EP91/02409, Dec. 13, 1991, abandoned.

[30] Foreign Application Priority Data

Dec. 14, 1990 [EP] European Pat. Off. ............. 90124241

[51] Int. Cl.$^6$ .................................................. G01N 33/576
[52] U.S. Cl. .............................. 435/5; 436/518; 436/820; 530/326
[58] Field of Search ........................... 435/5, 7.92, 7.95; 436/518, 820; 530/324, 326, 317

[56] References Cited

U.S. PATENT DOCUMENTS

| 5,106,726 | 4/1992 | Wang ........................................... 435/5 |
| 5,302,507 | 4/1994 | Chiba et al. .................................. 435/5 |
| 5,350,671 | 9/1994 | Houghton et al. ........................... 435/5 |

FOREIGN PATENT DOCUMENTS

| 0 318 216 | 5/1989 | European Pat. Off. . |
| 388232 | 9/1990 | European Pat. Off. . |
| 0 442 394 | 8/1991 | European Pat. Off. . |
| 0 445 423 | 9/1991 | European Pat. Off. . |
| 0 445 801 | 9/1991 | European Pat. Off. . |
| 0 450 931 | 10/1991 | European Pat. Off. . |
| 0 451 891 | 10/1991 | European Pat. Off. . |
| 0 468 527 | 1/1992 | European Pat. Off. . |
| 0 471 356 | 2/1992 | European Pat. Off. . |
| 0 484 787 | 5/1992 | European Pat. Off. . |
| WO 89/04669 | 6/1989 | WIPO . |
| WO 92/01714 | 2/1992 | WIPO . |

OTHER PUBLICATIONS

Vrancks, R., Evaluation of a line Immunoassay for the differential detection of antibodies to human Immunodeficiency virus. Eur. J. Clin. Microbiol. Infect. Dis. 9(9), 1990.

Shimonishi, Y., Ed., *Peptide Chemistry 1990, Proceedings of the 28th Symposium on Peptide Chemistry*, Osaka, Oct. 25–27, 1990. Munekata et al., "Epitope–Mapping of Hepatitis C Virus Constituting Protein," pp. 211–214, Protein Research Foundation, Osaka, 1991.

Choo, Q.L., et al, *Science* 244:359–362 (1989) "Isolation of a cDNA Clone Derived from a Blood–Borne Non–A, Non–B Viral Hepatitis Gnome".

Kuo, G., et al, *SCIENCE*, 244:362–364 (1989) "An Assay for Circulating Antibodies to a Major Etiologic Virus of Human Non–A, Non–B Hepatitis".

Okamoto, H., et al, *Japan J. Exp. Med.*, 60:3 167–177 (1990) "The 5'–Terminal Sequence of the Hepatitis C Virus Genome".

Okamoto, H., et al, *Japan J. Exp. Med.*, 60:4 223–233 (1990) "Enzyme–Linked Immunosorbent Assay for Antibodies against the Capsid Protein of Hepatitis C Virus with a Synthetic Oligopeptide".

*Primary Examiner*—Donna C. Wortman
*Attorney, Agent, or Firm*—Nixon & Vanderhye, P.C.

[57] ABSTRACT

Peptide sequences are provided which are capable of mimicking proteins encoded by HCV for use as reagents for screening of blood and blood products for prior exposure to HCV. The peptides are at least 5 amino acids long and can be used in various specific assays for the detection of antibodies to HCV, for the detection of HCV antigens, or as immunogens.

24 Claims, 8 Drawing Sheets

FIG.1A
Amino Acid Sequence of the Composite HCV$_{HC-J1/CDC/CHI}$

```
                         5                      10                     16
                         |                       |                      |
  1   Met Ser Thr Ile Pro Lys Pro Gln Arg Lys Thr Lys Arg Asn Thr Asn
 17   Arg Arg Pro Gln Asp Val Lys Phe Pro Gly Gly Gly Gln Ile Val Gly
 33   Gly Val Tyr Leu Leu Pro Arg Arg Gly Pro Arg Leu Gly Val Arg Ala
 49   Thr Arg Lys Thr Ser Glu Arg Ser Gln Pro Arg Gly Arg Arg Gln Pro
 65   Ile Pro Lys Val Arg Arg Pro Glu Gly Arg Thr Trp Ala Gln Pro Gly
 81   Tyr Pro Trp Pro Leu Tyr Gly Asn Glu Gly Cys Gly Trp Ala Gly Trp
 97   Leu Leu Ser Pro Arg Gly Ser Arg Pro Ser Trp Gly Pro Thr Asp Pro
113   Arg Arg Arg Ser Arg Asn Leu Gly Lys Val Ile Asp Thr Leu Thr Cys
129   Gly Phe Ala Asp Leu Met Gly Tyr Ile Pro Leu Val Gly Ala Pro Leu
145   Gly Gly Ala Ala Arg Ala Leu Ala His Gly Val Arg Val Leu Glu Asp
161   Gly Val Asn Tyr Ala Thr Gly Asn Leu Pro Gly Cys Ser Phe Ser Ile
177   Phe Leu Leu Ala Leu Leu Ser Cys Leu Thr Val Pro Ala Ser Ala Tyr
193   Gln Val Arg Asn Ser Thr Gly Leu Tyr His Val Thr Asn Asp Cys Pro
209   Asn Ser Ser Ile Val Tyr Glu Ala His Asp Ala Ile Leu His Thr Pro
225   Gly Cys Val Pro Cys Val Arg Glu Gly Asn Val Ser Arg Cys Trp Val
241   Ala Met Thr Pro Thr Val Ala Thr Arg Asp Gly Lys Leu Pro Ala Thr
257   Gln Leu Arg Arg His Ile Asp Leu Leu Val Gly Ser Ala Thr Leu Cys
273   Ser Ala Leu Tyr Val Gly Asp Leu Cys Gly Ser Val Phe Leu Ile Gly
289   Gln Leu Phe Thr Phe Ser Pro Arg Arg His Trp Thr Thr Gln Gly Cys
305   Asn Cys Ser Ile Tyr Pro Gly His Ile Thr Gly His Arg Met Ala Trp
321   Asp Met Met Met Asn Trp Ser Pro Thr Ala Ala Leu Val Met Ala Gln
337   Leu Leu Arg Ile Pro Gln Ala Ile Leu Asp Met Ile Ala Gly Ala His
353   Trp Gly Val Leu Ala Gly Ile Ala Tyr Phe Ser Met Val Gly Asn Trp
369   Ala Lys Val Leu Val Val Leu Leu Leu Phe Ala Gly Val Asp Ala Glu
385   Thr Ile Val Ser Gly Gly Gln Ala Ala Arg Ala Met Ser Gly Leu Val
401   Ser Leu Phe Thr Pro Gly Ala Lys Gln Asn Ile Gln Leu Ile Asn Thr
417   Asn Gly Ser Trp His Ile Asn Ser Thr Ala Leu Asn Cys Asn Glu Ser
433   Leu Asn Thr Gly Trp Leu Ala Gly Leu Ile Tyr Gln His Lys Phe Asn
449   Ser Ser Gly Cys Pro Glu Arg Leu Ala Ser Cys Arg Pro Leu Thr Asp
465   Phe Asp Gln Gly Trp Gly Pro Ile Ser Tyr Ala Asn Gly Ser Gly Pro
481   Asp Gln Arg Pro Tyr Cys Trp His Tyr Pro Pro Lys Pro Cys Gly Ile
497   Val Pro Ala Lys Ser Val Cys Gly Pro Val Tyr Cys Phe Thr Pro Ser
513   Pro Val Val Val Gly Thr Thr Asp Arg Ser Gly Ala Pro Thr Tyr Ser
529   Trp Gly Glu Asn Asp Thr Asp Val Phe Val Leu Asn Asn Thr Arg Pro
545   Pro Leu Gly Asn Trp Phe Gly Cys Thr Trp Met Asn Ser Thr Gly Phe
561   Thr Lys Val Cys Gly Ala Pro Pro Cys Val Ile Gly Gly Ala Gly Asn
577   Asn Thr Leu His Cys Pro Thr Asp Cys Phe Arg Lys His Pro Asp Ala
593   Thr Tyr Ser Arg Cys Gly Ser Gly Pro Trp Ile Thr Pro Arg Cys Leu
609   Val Asp Tyr Pro Tyr Arg Leu Trp His Tyr Pro Cys Thr Ile Asn Tyr
625   Thr Ile Phe Lys Ile Arg Met Tyr Val Gly Gly Val Glu His Arg Leu
641   Glu Ala Ala Cys Asn Trp Thr Arg Gly Glu Arg Cys Asp Leu Glu Asp
657   Arg Asp Arg Ser Glu Leu Ser Pro Leu Leu Leu Thr Thr Thr Gln Trp
673   Gln Val Leu Pro Cys Ser Phe Thr Thr Leu Pro Ala Leu Ser Thr Gly
689   Leu Ile His Leu His Gln Asn Ile Val Asp Val Gln Tyr Leu Tyr Gly
705   Val Gly Ser Ser Ile Ala Ser Trp Ala Ile Lys Trp Glu Tyr Val Val
```

FIG.1B

```
 721  Leu Leu Phe Leu Leu Leu Ala Asp Ala Arg Val Cys Ser Cys Leu Trp
 737  Met Met Leu Leu Ile Ser Gln Ala Glu Ala Ala Leu Glu Asn Leu Val
 753  Ile Leu Asn Ala Ala Ser Leu Ala Gly Thr His Gly Leu Val Ser Phe
 769  Leu Val Phe Phe Cys Phe Ala Trp Tyr Leu Lys Gly Lys Trp Val Pro
 785  Gly Ala Val Tyr Thr Phe Tyr Gly Met Trp Pro Leu Leu Leu Leu Leu
 801  Leu Ala Leu Pro Gln Arg Ala Tyr Ala Leu Asp Thr Glu Val Ala Ala
 817  Ser Cys Gly Gly Val Val Leu Val Gly Leu Met Ala Leu Thr Leu Ser
 833  Pro Tyr Tyr Lys Arg Tyr Ile Ser Trp Cys Leu Trp Trp Leu Gln Tyr
 849  Phe Leu Thr Arg Val Glu Ala Gln Leu His Val Trp Ile Pro Pro Leu
 865  Asn Val Arg Gly Gly Arg Asp Ala Val Ile Leu Leu Met Cys Ala Val
 881  His Pro Thr Leu Val Phe Asp Ile Thr Lys Leu Leu Leu Ala Val Phe
 897  Gly Pro Leu Trp Ile Leu Asp Ala Ser Leu Leu Lys Val Pro Tyr Phe
 913  Val Arg Val Gln Gly Leu Leu Arg Phe Cys Ala Leu Ala Arg Lys Met
 929  Ile Gly Gly His Tyr Val Gln Met Val Ile Ile Lys Leu Gly Ala Leu
 945  Thr Gly Thr Tyr Val Tyr Asn His Leu Thr Pro Leu Arg Asp Trp Ala
 961  His Asn Gly Leu Arg Asp Leu Ala Val Ala Val Glu Pro Val Val Phe
 977  Ser Gln Met Glu Thr Lys Leu Ile Thr Trp Gly Ala Asp Thr Ala Ala
 993  Cys Gly Asp Ile Ile Asn Gly Leu Pro Val Ser Ala Arg Arg Gly Arg
1009  Glu Ile Leu Leu Gly Pro Ala Asp Gly Met Val Ser Lys Gly Trp Arg
1025  Leu Leu Ala Pro Ile Thr Ala Tyr Ala Gln Gln Thr Arg Gly Leu Leu
1041  Gly Cys Ile Ile Thr Ser Leu Thr Gly Arg Asp Lys Asn Gln Val Glu
1057  Gly Glu Val Gln Ile Val Ser Thr Ala Ala Gln Thr Phe Leu Ala Thr
1073  Cys Ile Asn Gly Val Cys Trp Thr Val Tyr His Gly Ala Gly Thr Arg
1089  Thr Ile Ala Ser Pro Lys Gly Pro Val Ile Gln Met Tyr Thr Asn Val
1105  Asp Gln Asp Leu Val Gly Trp Pro Ala Pro Gln Gly Ser Arg Ser Leu
1121  Thr Pro Cys Thr Cys Gly Ser Ser Asp Leu Tyr Leu Val Thr Arg His
1137  Ala Asp Val Ile Pro Val Arg Arg Arg Gly Asp Ser Arg Gly Ser Leu
1153  Leu Ser Pro Arg Pro Ile Ser Tyr Leu Lys Gly Ser Ser Gly Gly Pro
1169  Leu Leu Cys Pro Ala Gly His Ala Val Gly Ile Phe Arg Ala Ala Val
1185  Cys Thr Arg Gly Val Ala Lys Ala Val Asp Phe Ile Pro Val Glu Asn
1201  Leu Glu Thr Thr Met Arg Ser Pro Val Phe Trp Asp Asn Ser Ser Pro
1217  Pro Val Val Pro Gln Ser Phe Gln Val Ala His Leu His Ala Pro Thr
1233  Gly Ser Gly Lys Ser Thr Lys Val Pro Ala Ala Tyr Ala Ala Gln Gly
1249  Tyr Lys Val Leu Val Leu Asn Pro Ser Val Ala Ala Thr Leu Gly Phe
1265  Gly Ala Tyr Met Ser Lys Ala His Gly Ile Asp Pro Asn Ile Arg Thr
1281  Gly Val Arg Thr Ile Thr Thr Gly Ser Pro Ile Thr Tyr Ser Thr Tyr
1297  Gly Lys Phe Leu Ala Asp Gly Gly Cys Ser Gly Gly Ala Tyr Asp Ile
1313  Ile Ile Cys Asp Glu Cys His Ser Thr Asp Ala Thr Ser Ile Leu Gly
1329  Ile Gly Thr Val Leu Asp Gln Ala Glu Thr Ala Gly Ala Arg Leu Val
1345  Val Leu Ala Thr Ala Thr Pro Pro Gly Ser Val Thr Val Pro His Pro
1361  Asn Ile Glu Glu Val Ala Leu Ser Thr Thr Gly Glu Ile Pro Phe Tyr
1377  Gly Lys Ala Ile Pro Leu Glu Val Ile Lys Gly Gly Arg His Leu Ile
1393  Phe Cys His Ser Lys Lys Lys Cys Asp Glu Leu Ala Ala Lys Leu Val
1409  Ala Leu Gly Ile Asn Ala Val Ala Tyr Tyr Arg Gly Leu Asp Val Ser
1425  Val Ile Pro Thr Ser Gly Asp Val Val Val Val Ala Thr Asp Ala Leu
```

FIG.1C

```
1441  Met Thr Gly Tyr Thr Gly Asp Phe Asp Ser Val Ile Asp Cys Asn Thr
1457  Cys Val Thr Gln Thr Val Asp Phe Ser Leu Asp Pro Thr Phe Thr Ile
1473  Glu Thr Ile Thr Leu Pro Gln Asp Ala Val Ser Arg Thr Gln Arg Arg
1489  Gly Arg Thr Gly Arg Gly Lys Pro Gly Ile Tyr Arg Phe Val Ala Pro
1505  Gly Glu Arg Pro Ser Gly Met Phe Asp Ser Ser Val Leu Cys Glu Cys
1521  Tyr Asp Ala Gly Cys Ala Trp Tyr Glu Leu Thr Pro Ala Glu Thr Thr
1537  Val Arg Leu Arg Ala Tyr Met Asn Thr Pro Gly Leu Pro Val Cys Gln
1553  Asp His Leu Glu Phe Trp Glu Gly Val Phe Thr Gly Leu Thr His Ile
1569  Asp Ala His Phe Leu Ser Gln Thr Lys Gly Ser Gly Glu Asn Leu Pro
1585  Tyr Leu Val Ala Tyr Gln Ala Thr Val Cys Ala Arg Ala Gln Ala Pro
1601  Pro Pro Ser Trp Asp Gln Met Trp Lys Cys Leu Ile Arg Leu Lys Pro
1617  Thr Leu His Gly Pro Thr Pro Leu Leu Tyr Arg Leu Gly Ala Val Gln
1633  Asn Glu Ile Thr Leu Thr His Pro Val Thr Lys Tyr Ile Met Thr Cys
1649  Met Ser Ala Asp Leu Glu Val Val Thr Ser Thr Trp Val Leu Val Gly
1665  Gly Val Leu Ala Ala Leu Ala Ala Tyr Cys Leu Ser Thr Gly Cys Val
1681  Val Ile Val Gly Arg Val Val Leu Ser Gly Lys Pro Ala Ile Ile Pro
1697  Asp Arg Glu Val Leu Tyr Arg Glu Phe Asp Glu Met Glu Glu Cys Ser
1713  Gln His Leu Pro Tyr Ile Glu Gln Gly Met Met Leu Ala Glu Gln Phe
1729  Lys Gln Lys Ala Leu Gly Leu Leu Gln Thr Ala Ser Arg Gln Ala Glu
1745  Val Ile Ala Pro Ala Val Gln Thr Asn Trp Gln Lys Leu Glu Thr Phe
1761  Trp Ala Lys His Met Trp Asn Phe Ile Ser Gly Ile Gln Tyr Leu Ala
1777  Gly Leu Ser Thr Leu Pro Gly Asn Pro Ala Ile Ala Ser Leu Met Ala
1793  Phe Thr Ala Ala Val Thr Ser Pro Leu Thr Thr Ser Gln Thr Leu Leu
1809  Phe Asn Ile Leu Gly Gly Trp Val Ala Ala Gln Leu Ala Ala Pro Gly
1825  Ala Ala Thr Ala Phe Val Gly Ala Gly Leu Ala Gly Ala Ala Ile Gly
1841  Ser Val Gly Leu Gly Lys Val Leu Ile Asp Ile Leu Ala Gly Tyr Gly
1857  Ala Gly Val Ala Gly Ala Leu Val Ala Phe Lys Ile Met Ser Gly Glu
1873  Val Pro Ser Thr Glu Asp Leu Val Asn Leu Leu Pro Ala Ile Leu Ser
1889  Pro Gly Ala Leu Val Val Gly Val Val Cys Ala Ala Ile Leu Arg Arg
1905  His Val Gly Pro Gly Glu Gly Ala Val Gln Trp Met Asn Arg Leu Ile
1921  Ala Phe Ala Ser Arg Gly Asn His Val Ser Pro Thr His Tyr Val Pro
1937  Glu Ser Asp Ala Ala Ala Arg Val Thr Ala Ile Leu Ser Ser Leu Thr
1953  Val Thr Gln Leu Leu Arg Arg Leu His Gln Trp Ile Ser Ser Glu Cys
1969  Thr Thr Pro Cys Ser Gly Ser Trp Leu Arg Asp Ile Trp Asp Trp Ile
1985  Cys Glu Val Leu Ser Asp Phe Lys Thr Trp Leu Lys Ala Lys Leu Met
2001  Pro Gln Leu Pro Gly Ile Pro Phe Val Ser Cys Gln Arg Gly Tyr Lys
2017  Gly Val Trp Arg Val Asp Gly Ile Met His Thr Arg Cys His Cys Gly
2033  Ala Glu Ile Thr Gly His Val Lys Asn Gly Thr Met Arg Ile Val Gly
2049  Pro Arg Thr Cys Arg Asn Met Trp Ser Gly Thr Phe Pro Ile Asn Ala
2065  Tyr Thr Thr Gly Pro Cys Thr Arg Leu Pro Ala Pro Asn Tyr Thr Phe
2081  Ala Leu Trp Arg Val Ser Ala Glu Glu Tyr Val Glu Ile Arg Gln Val
2097  Gly Asp Phe His Tyr Val Thr Gly Met Thr Thr Asp Asn Leu Lys Cys
2113  Pro Cys Gln Val Pro Ser Pro Glu Phe Phe Thr Glu Leu Asp Gly Val
2129  Arg Leu His Arg Phe Ala Pro Pro Cys Lys Pro Leu Leu Arg Glu Glu
2145  Val Ser Phe Arg Val Gly Leu His Glu Tyr Pro Val Gly Ser Gln Leu
```

FIG.1D

```
2161  Pro Cys Glu Pro Glu Pro Asp Val Ala Val Leu Thr Ser Met Leu Thr
2177  Asp Pro Ser His Ile Thr Ala Glu Ala Ala Gly Arg Arg Leu Ala Arg
2193  Gly Ser Pro Pro Ser Val Ala Ser Ser Ser Ala Ser Gln Leu Ser Ala
2209  Pro Ser Leu Lys Ala Thr Cys Thr Ala Asn His Asp Ser Pro Asp Ala
2225  Glu Leu Ile Glu Ala Asn Leu Leu Trp Arg Gln Glu Met Gly Gly Asn
2241  Ile Thr Arg Val Glu Ser Glu Asn Lys Val Val Ile Leu Asp Ser Phe
2257  Asp Pro Leu Val Ala Glu Glu Asp Glu Arg Glu Ile Ser Val Pro Ala
2273  Glu Ile Leu Arg Lys Ser Arg Arg Phe Ala Gln Ala Leu Pro Val Trp
2289  Ala Arg Pro Asp Tyr Asn Pro Pro Leu Val Glu Thr Trp Lys Lys Pro
2305  Asp Tyr Glu Pro Pro Val Val His Gly Cys Pro Leu Pro Pro Pro Lys
2321  Ser Pro Pro Val Pro Pro Pro Arg Lys Lys Arg Thr Val Val Leu Thr
2337  Glu Ser Thr Leu Ser Thr Ala Leu Ala Glu Leu Ala Thr Arg Ser Phe
2353  Gly Ser Ser Ser Thr Ser Gly Ile Thr Gly Asp Asn Thr Thr Thr Ser
2369  Ser Glu Pro Ala Pro Ser Gly Cys Pro Pro Asp Ser Asp Ala Glu Ser
2385  Tyr Ser Ser Met Pro Pro Leu Glu Gly Glu Pro Gly Asp Pro Asp Leu
2401  Ser Asp Gly Ser Trp Ser Thr Val Ser Ser Glu Ala Asn Ala Glu Asp
2417  Val Val Cys Cys Ser Met Ser Tyr Ser Trp Thr Gly Ala Cys Val Thr
2433  Pro Cys Ala Ala Glu Glu Gln Lys Leu Pro Ile Asn Ala Leu Ser Asn
2449  Ser Leu Leu Arg His His Asn Leu Val Tyr Ser Thr Thr Ser Arg Ser
2465  Ala Cys Gln Arg Gln Lys Lys Val Thr Phe Asp Arg Leu Gln Val Leu
2481  Asp Ser His Tyr Gln Asp Val Leu Lys Glu Val Lys Ala Ala Ala Ser
2497  Lys Val Lys Ala Asn Leu Leu Ser Val Glu Glu Ala Cys Ser Leu Thr
2513  Pro Pro His Ser Ala Lys Ser Lys Phe Gly Tyr Gly Ala Lys Asp Val
2529  Arg Cys His Ala Arg Lys Ala Val Thr His Ile Asn Ser Val Trp Lys
2545  Asp Leu Leu Glu Asp Asn Val Thr Pro Ile Asp Thr Thr Ile Met Ala
2561  Lys Asn Glu Val Phe Cys Val Gln Pro Glu Lys Gly Gly Arg Lys Pro
2577  Ala Arg Leu Ile Val Phe Pro Asp Leu Gly Val Arg Val Cys Glu Lys
2593  Met Ala Leu Tyr Asp Val Val Thr Lys Leu Pro Leu Ala Val Met Gly
2609  Ser Ser Tyr Gly Phe Gln Tyr Ser Pro Gly Gln Arg Val Glu Phe Leu
2625  Val Gln Ala Trp Lys Ser Lys Lys Thr Pro Met Gly Phe Ser Tyr Asp
2641  Thr Arg Cys Phe Asp Ser Thr Val Thr Glu Ser Asp Ile Arg Thr Glu
2657  Glu Ala Ile Tyr Gln Cys Cys Asp Leu Asp Pro Gln Ala Arg Val Ala
2673  Ile Lys Ser Leu Thr Glu Arg Leu Tyr Val Gly Gly Pro Leu Thr Asn
2689  Ser Arg Gly Glu Asn Cys Gly Tyr Arg Arg Cys Arg Ala Ser Gly Val
2705  Leu Thr Thr Ser Cys Gly Asn Thr Leu Thr Cys Tyr Ile Lys Ala Arg
2721  Ala Ala Cys Arg Ala Ala Gly Leu Gln Asp Cys Thr Met Leu Val Cys
2737  Gly Asp Asp Leu Val Val Ile Cys Glu Ser Ala Gly Val Gln Glu Asp
2753  Ala Ala Ser Leu Arg Ala Phe Thr Glu Ala Met Thr Arg Tyr Ser Ala
2769  Pro Pro Gly Asp Pro Pro Gln Pro Glu Tyr Asp Leu Glu Leu Ile Thr
2785  Ser Cys Ser Ser Asn Val Ser Val Ala His Asp Gly Ala Gly Lys Arg
2801  Val Tyr Tyr Leu Thr Arg Asp Pro Thr Thr Pro Leu Ala Arg Ala Ala
2817  Trp Glu Thr Ala Arg His Thr Pro Val Asn Ser Trp Leu Gly Asn Ile
2833  Ile Met Phe Ala Pro Thr Leu Trp Ala Arg Met Ile Leu Met Thr His
2849  Phe Phe Ser Val Leu Ile Ala Arg Asp Gln Leu Glu Gln Ala Leu Asp
2865  Cys Glu Ile Tyr Gly Ala Cys Tyr Ser Ile Glu Pro Leu Asp Leu Pro
2881  Pro Ile Ile Gln Arg Leu Gly Cys Pro Glu Arg Leu Ala Ser
```

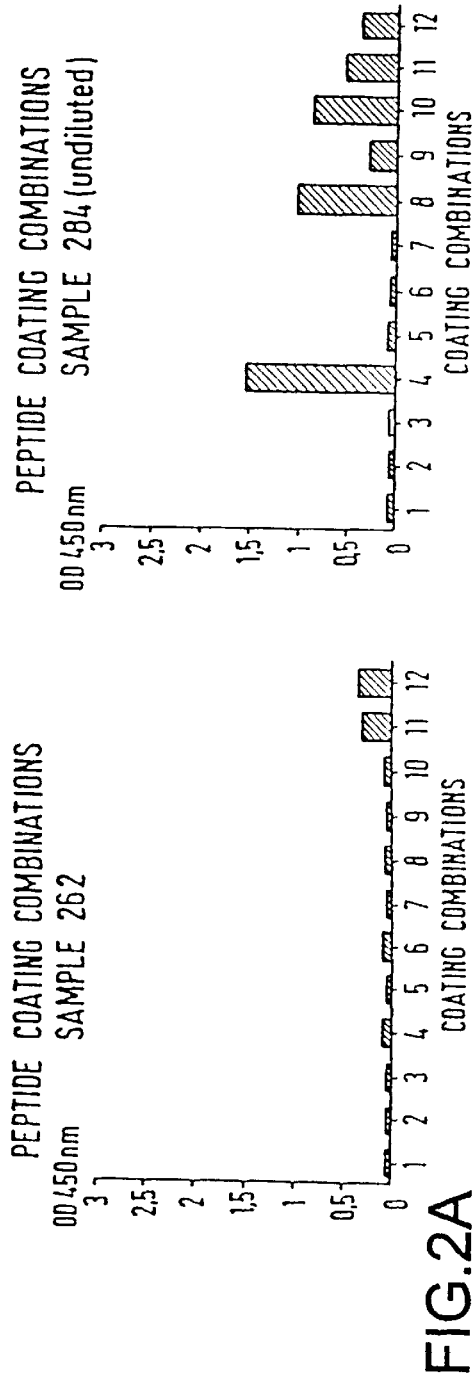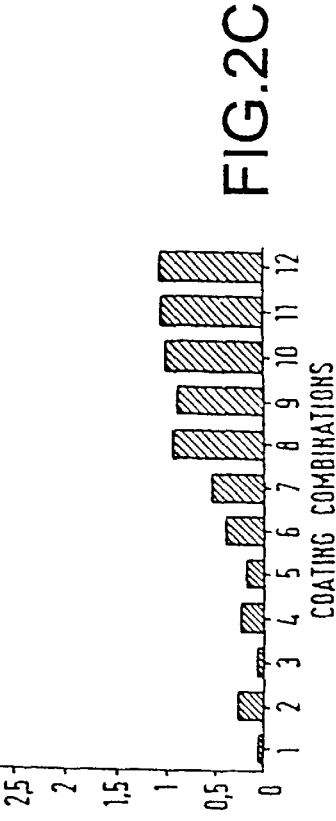

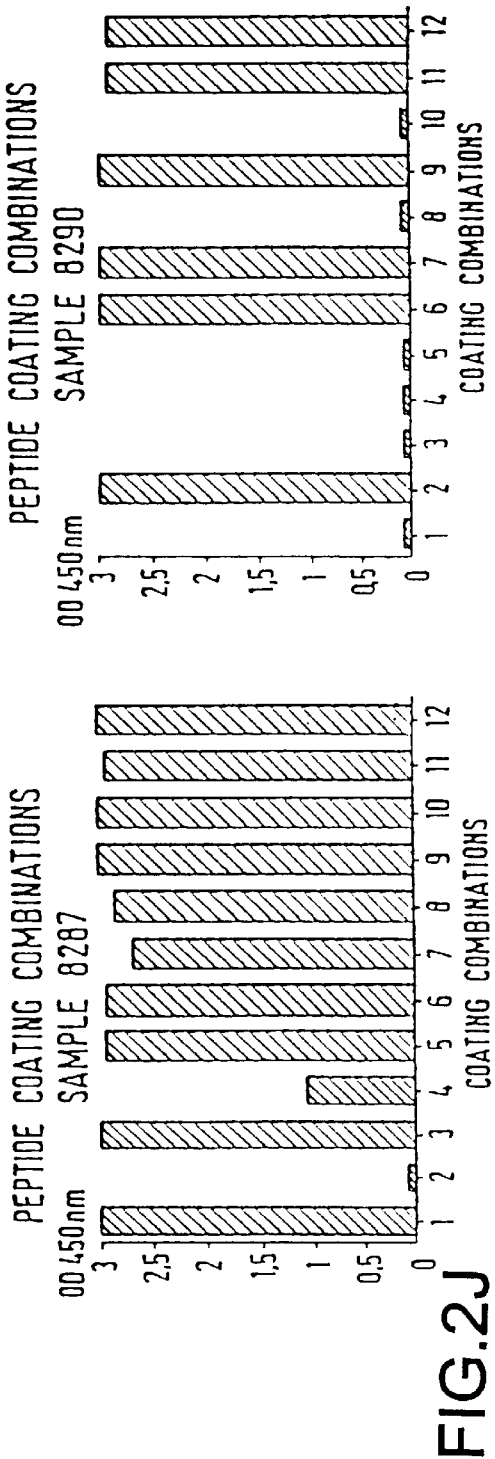
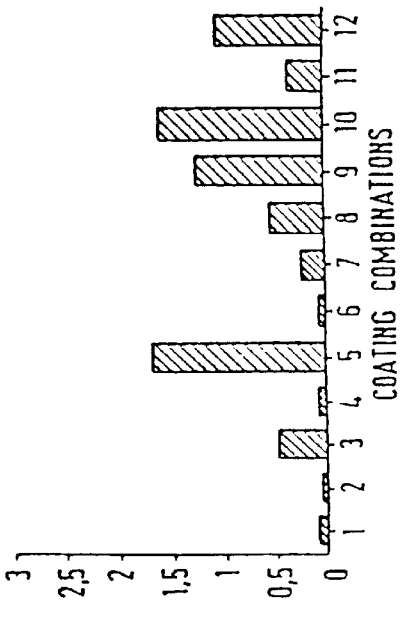
FIG.2J
FIG.2K
FIG.2L

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:1:

Met Ser Thr Ile Pro Lys Pro Gln Arg Lys Thr Lys Arg Asn Thr Asn
1               5                   10                  15

Arg Arg Pro Gln
            20

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Pro Gln Arg Lys Thr Lys Arg Asn Thr Asn Arg Arg Pro Gln Asp Val
1               5                   10                  15

Lys Phe Pro Gly
            20

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gln Arg Lys Thr Lys Arg Asn Thr Asn Arg Arg
1               5                   10

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Arg Asn Thr Asn Arg Arg Pro Gln Asp Val Lys Phe Pro Gly Gly Gly
1               5                   10                  15

Gln Ile Val Gly
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Leu Pro Arg Arg Gly Pro Arg Leu Gly Val Arg Ala Thr Arg Lys Thr
    1               5                   10                  15

Ser Glu Arg Ser
                20

(2) INFORMATION FOR SEQ ID NO:6:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Thr Arg Lys Thr Ser Glu Arg Ser Gln Pro Arg Gly Arg Arg Gln Pro
    1               5                   10                  15

Ile Pro Lys Val
                20

(2) INFORMATION FOR SEQ ID NO:7:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Arg Arg Gln Pro Ile Pro Lys Val Arg Arg Pro Glu Gly Arg Thr Trp
    1               5                   10                  15

Ala Gln Pro Gly
                20

(2) INFORMATION FOR SEQ ID NO:8:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Gly Arg Thr Trp Ala Gln Pro Gly Tyr Pro Trp Pro Leu Tyr Gly Asn
    1               5                   10                  15

Glu Gly Cys Gly
                20

(2) INFORMATION FOR SEQ ID NO:9:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

```
Leu Ser Gly Lys Pro Ala Ile Ile Pro Asp Arg Glu Val Leu Tyr Arg
1               5                   10                  15

Glu Phe Asp Glu
            20
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Ile Ile Pro Asp Arg Glu Val Leu Tyr Arg Glu Phe Asp Glu Met Glu
1               5                   10                  15

Glu Cys Ser Gln
            20
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Asp Glu Met Glu Glu Cys Ser Gln His Leu Pro Tyr Ile Glu Gln Gly
1               5                   10                  15

Met Met Leu Ala
            20
```

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Ser Gln His Leu Pro Tyr Ile Glu Gln Gly Met Met Leu Ala Glu Gln
1               5                   10                  15

Phe Lys Gln Lys
            20
```

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Ile Glu Gln Gly Met Met Leu Ala Glu Gln Phe Lys Gln Lys Ala Leu
1               5                   10                  15

Gly Leu Leu Gln
```

```
            20

(2) INFORMATION FOR SEQ ID NO:14:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:14:

Leu Ala Glu Gln Phe Lys Gln Lys Ala Leu Gly Leu Leu Gln Thr Ala
    1               5                  10                  15

Ser Arg Gln Ala
                20

(2) INFORMATION FOR SEQ ID NO:15:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:15:

Gln Lys Ala Leu Gly Leu Leu Gln Thr Ala Ser Arg Gln Ala Glu Val
    1               5                  10                  15

Ile Ala Pro Ala
                20

(2) INFORMATION FOR SEQ ID NO:16:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:16:

Glu Asp Glu Arg Glu Ile Ser Val Pro Ala Glu Ile Leu Arg Lys Ser
    1               5                  10                  15

Arg Arg Phe Ala
                20

(2) INFORMATION FOR SEQ ID NO:17:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:17:

Leu Arg Lys Ser Arg Arg Phe Ala Gln Ala Leu Pro Val Trp Ala Arg
    1               5                  10                  15

Pro Asp Tyr Asn
                20

(2) INFORMATION FOR SEQ ID NO:18:
```

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Val Trp Ala Arg Pro Asp Tyr Asn Pro Pro Leu Val Glu Thr Trp Lys
1               5                   10                  15

Lys Pro Asp Tyr
            20

(2) INFORMATION FOR SEQ ID NO:19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Glu Thr Trp Lys Lys Pro Asp Tyr Glu Pro Pro Val Val His Gly Cys
    1               5                   10                  15

Pro Leu Pro Pro
                20

(2) INFORMATION FOR SEQ ID NO:20:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Val His Gly Cys Pro Leu Pro Pro Lys Ser Pro Val Pro Pro
    1               5                   10                  15

Pro Arg Lys Lys
                20

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Glu Arg Glu Ile Ser Val Pro Ala Glu Ile Leu Arg Lys Ser Arg Arg
    1               5                   10                  15

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Arg Phe Ala Gln Ala Leu Pro Val Trp Ala Arg
1               5                   10
```

(2) INFORMATION FOR SEQ ID NO: 23:

(i) SEQUENCE CHARACTERISTICS:
       (A) LENGTH: 2894 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 23:

```
Met Ser Thr Ile Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Val Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala His Asp Ala Ile Leu His Thr Pro
210                 215                 220

Gly Cys Val Pro Cys Val Arg Glu Gly Asn Val Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Ile Gly
        275                 280                 285

Gln Leu Phe Thr Phe Ser Pro Arg Arg His Trp Thr Thr Gln Gly Cys
290                 295                 300
```

```
Asn Cys Ser Ile Tyr Pro Gly His Ile Thr Gly His Arg Met Ala Trp
305                 310                 315                 320

Asp Met Met Asn Trp Ser Pro Thr Ala Ala Leu Val Met Ala Gln
            325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr Ile Val Ser Gly Gln Ala Ala Arg Ala Met Ser Gly Leu Val
385                 390                 395                 400

Ser Leu Phe Thr Pro Gly Ala Lys Gln Asn Ile Gln Leu Ile Asn Thr
            405                 410                 415

Asn Gly Ser Trp His Ile Asn Ser Thr Ala Leu Asn Cys Asn Glu Ser
        420                 425                 430

Leu Asn Thr Gly Trp Leu Ala Gly Leu Ile Tyr Gln His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
            485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
            565                 570                 575

Asn Thr Leu His Cys Pro Thr Asp Cys Phe Arg Lys His Pro Asp Ala
        580                 585                 590

Thr Tyr Ser Arg Cys Gly Ser Gly Pro Trp Ile Thr Pro Arg Cys Leu
    595                 600                 605

Val Asp Tyr Pro Tyr Arg Leu Trp His Tyr Pro Cys Thr Ile Asn Tyr
610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
            645                 650                 655

Arg Asp Arg Ser Glu Leu Ser Pro Leu Leu Leu Thr Thr Thr Gln Trp
        660                 665                 670

Gln Val Leu Pro Cys Ser Phe Thr Thr Leu Pro Ala Leu Ser Thr Gly
    675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
```

-continued

```
            725                 730                 735
Met Met Leu Leu Ile Ser Gln Ala Glu Ala Ala Leu Glu Asn Leu Val
            740                 745                 750
Ile Leu Asn Ala Ala Ser Leu Ala Gly Thr His Gly Leu Val Ser Phe
            755                 760                 765
Leu Val Phe Phe Cys Phe Ala Trp Tyr Leu Lys Gly Lys Trp Val Pro
            770                 775                 780
Gly Ala Val Tyr Thr Phe Tyr Gly Met Trp Pro Leu Leu Leu Leu
785                 790                 795                 800
Leu Ala Leu Pro Gln Arg Ala Tyr Ala Leu Asp Thr Glu Val Ala Ala
            805                 810                 815
Ser Cys Gly Gly Val Val Leu Val Gly Leu Met Ala Leu Thr Leu Ser
            820                 825                 830
Pro Tyr Tyr Lys Arg Tyr Ile Ser Trp Cys Leu Trp Trp Leu Gln Tyr
            835                 840                 845
Phe Leu Thr Arg Val Glu Ala Gln Leu His Val Trp Ile Pro Pro Leu
            850                 855                 860
Asn Val Arg Gly Gly Arg Asp Ala Val Ile Leu Leu Met Cys Ala Val
865                 870                 875                 880
His Pro Thr Leu Val Phe Asp Ile Thr Lys Leu Leu Leu Ala Val Phe
            885                 890                 895
Gly Pro Leu Trp Ile Leu Asp Ala Ser Leu Leu Lys Val Pro Tyr Phe
            900                 905                 910
Val Arg Val Gln Gly Leu Leu Arg Phe Cys Ala Leu Ala Arg Lys Met
            915                 920                 925
Ile Gly Gly His Tyr Val Gln Met Val Ile Lys Leu Gly Ala Leu
            930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Val Phe
            965                 970                 975
Ser Gln Met Glu Thr Lys Leu Ile Thr Trp Gly Ala Asp Thr Ala Ala
            980                 985                 990
Cys Gly Asp Ile Ile Asn Gly Leu Pro Val Ser Ala Arg Arg Gly Arg
            995                 1000                1005
Glu Ile Leu Leu Gly Pro Ala Asp Gly Met Val Ser Lys Gly Trp Arg
1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
            1045                1050                1055
Gly Glu Val Gln Ile Val Ser Thr Ala Ala Gln Thr Phe Leu Ala Thr
            1060                1065                1070
Cys Ile Asn Gly Val Cys Trp Thr Val Tyr His Gly Ala Gly Thr Arg
            1075                1080                1085
Thr Ile Ala Ser Pro Lys Gly Pro Val Ile Gln Met Tyr Thr Asn Val
            1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
            1125                1130                1135
Ala Asp Val Ile Pro Val Arg Arg Arg Gly Asp Ser Arg Gly Ser Leu
            1140                1145                1150
```

```
Leu Ser Pro Arg Pro Ile Ser Tyr Leu Lys Gly Ser Ser Gly Pro
        1155                1160                1165

Leu Leu Cys Pro Ala Gly His Ala Val Gly Ile Phe Arg Ala Val
        1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Trp Asp Asn Ser Ser Pro
                1205                1210                1215

Pro Val Val Pro Gln Ser Phe Gln Val Ala His Leu His Ala Pro Thr
                1220                1225                1230

Gly Ser Gly Lys Ser Thr Lys Val Pro Ala Ala Tyr Ala Ala Gln Gly
                1235                1240                1245

Tyr Lys Val Leu Val Leu Asn Pro Ser Val Ala Ala Thr Leu Gly Phe
        1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
                1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
                1380                1385                1390

Phe Cys His Ser Lys Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
                1460                1465                1470

Glu Thr Ile Thr Leu Pro Gln Asp Ala Val Ser Arg Thr Gln Arg Arg
        1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
                1525                1530                1535

Val Arg Leu Arg Ala Tyr Met Asn Thr Pro Gly Leu Pro Val Cys Gln
        1540                1545                1550

Asp His Leu Glu Phe Trp Glu Gly Val Phe Thr Gly Leu Thr His Ile
        1555                1560                1565

Asp Ala His Phe Leu Ser Gln Thr Lys Gly Ser Gly Glu Asn Leu Pro
        1570                1575                1580
```

```
Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
        1620                1625                1630

Asn Glu Ile Thr Leu Thr His Pro Val Thr Lys Tyr Ile Met Thr Cys
    1635                1640                1645

Met Ser Ala Asp Leu Glu Val Val Thr Ser Thr Trp Val Leu Val Gly
1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
                1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg Gln Ala Glu
    1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
        1795                1800                1805

Phe Asn Ile Leu Gly Gly Trp Val Ala Ala Gln Leu Ala Ala Pro Gly
    1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
                1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
        1955                1960                1965

Thr Thr Pro Cys Ser Gly Ser Trp Leu Arg Asp Ile Trp Asp Trp Ile
    1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
```

-continued

```
            2005                2010                2015
Gly Val Trp Arg Val Asp Gly Ile Met His Thr Arg Cys His Cys Gly
            2020                2025                2030
Ala Glu Ile Thr Gly His Val Lys Asn Gly Thr Met Arg Ile Val Gly
            2035                2040                2045
Pro Arg Thr Cys Arg Asn Met Trp Ser Gly Thr Phe Pro Ile Asn Ala
            2050                2055                2060
Tyr Thr Thr Gly Pro Cys Thr Arg Leu Pro Ala Pro Asn Tyr Thr Phe
2065                2070                2075                2080
Ala Leu Trp Arg Val Ser Ala Glu Glu Tyr Val Glu Ile Arg Gln Val
            2085                2090                2095
Gly Asp Phe His Tyr Val Thr Gly Met Thr Thr Asp Asn Leu Lys Cys
            2100                2105                2110
Pro Cys Gln Val Pro Ser Pro Glu Phe Phe Thr Glu Leu Asp Gly Val
            2115                2120                2125
Arg Leu His Arg Phe Ala Pro Pro Cys Lys Pro Leu Leu Arg Glu Glu
            2130                2135                2140
Val Ser Phe Arg Val Gly Leu His Glu Tyr Pro Val Gly Ser Gln Leu
2145                2150                2155                2160
Pro Cys Glu Pro Glu Pro Asp Val Ala Val Leu Thr Ser Met Leu Thr
            2165                2170                2175
Asp Pro Ser His Ile Thr Ala Glu Ala Ala Gly Arg Arg Leu Ala Arg
            2180                2185                2190
Gly Ser Pro Pro Ser Val Ala Ser Ser Ser Ala Ser Gln Leu Ser Ala
            2195                2200                2205
Pro Ser Leu Lys Ala Thr Cys Thr Ala Asn His Asp Ser Pro Asp Ala
            2210                2215                2220
Glu Leu Ile Glu Ala Asn Leu Leu Trp Arg Gln Glu Met Gly Gly Asn
2225                2230                2235                2240
Ile Thr Arg Val Glu Ser Glu Asn Lys Val Val Ile Leu Asp Ser Phe
            2245                2250                2255
Asp Pro Leu Val Ala Glu Glu Asp Glu Arg Glu Ile Ser Val Pro Ala
            2260                2265                2270
Glu Ile Leu Arg Lys Ser Arg Arg Phe Ala Gln Ala Leu Pro Val Trp
            2275                2280                2285
Ala Arg Pro Asp Tyr Asn Pro Pro Leu Val Glu Thr Trp Lys Lys Pro
            2290                2295                2300
Asp Tyr Glu Pro Pro Val Val His Gly Cys Pro Leu Pro Pro Pro Lys
2305                2310                2315                2320
Ser Pro Pro Val Pro Pro Pro Arg Lys Lys Arg Thr Val Val Leu Thr
            2325                2330                2335
Glu Ser Thr Leu Ser Thr Ala Leu Ala Glu Leu Ala Thr Arg Ser Phe
            2340                2345                2350
Gly Ser Ser Ser Thr Ser Gly Ile Thr Gly Asp Asn Thr Thr Thr Ser
            2355                2360                2365
Ser Glu Pro Ala Pro Ser Gly Cys Pro Pro Asp Ser Asp Ala Glu Ser
            2370                2375                2380
Tyr Ser Ser Met Pro Pro Leu Glu Gly Glu Pro Gly Asp Pro Asp Leu
2385                2390                2395                2400
Ser Asp Gly Ser Trp Ser Thr Val Ser Ser Glu Ala Asn Ala Glu Asp
            2405                2410                2415
Val Val Cys Cys Ser Met Ser Tyr Ser Trp Thr Gly Ala Cys Val Thr
            2420                2425                2430
```

-continued

```
Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
        2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
                2485                2490                2495

Lys Val Lys Ala Asn Leu Leu Ser Val Glu Glu Ala Cys Ser Leu Thr
                2500                2505                2510

Pro Pro His Ser Ala Lys Ser Lys Phe Gly Tyr Gly Ala Lys Asp Val
                2515                2520                2525

Arg Cys His Ala Arg Lys Ala Val Thr His Ile Asn Ser Val Trp Lys
                2530                2535                2540

Asp Leu Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
                2580                2585                2590

Met Ala Leu Tyr Asp Val Val Thr Lys Leu Pro Leu Ala Val Met Gly
                2595                2600                2605

Ser Ser Tyr Gly Phe Gln Tyr Ser Pro Gly Gln Arg Val Glu Phe Leu
                2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
                2660                2665                2670

Ile Lys Ser Leu Thr Glu Arg Leu Tyr Val Gly Gly Pro Leu Thr Asn
                2675                2680                2685

Ser Arg Gly Glu Asn Cys Gly Tyr Arg Arg Cys Arg Ala Ser Gly Val
                2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
                2740                2745                2750

Ala Ala Ser Leu Arg Ala Phe Thr Glu Ala Met Thr Arg Tyr Ser Ala
                2755                2760                2765

Pro Pro Gly Asp Pro Pro Gln Pro Glu Tyr Asp Leu Glu Leu Ile Thr
                2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
                2820                2825                2830

Ile Met Phe Ala Pro Thr Leu Trp Ala Arg Met Ile Leu Met Thr His
                2835                2840                2845

Phe Phe Ser Val Leu Ile Ala Arg Asp Gln Leu Glu Gln Ala Leu Asp
                2850                2855                2860
```

```
Cys Glu Ile Tyr Gly Ala Cys Tyr Ser Ile Glu Pro Leu Asp Leu Pro
2865             2870            2875            2880

Pro Ile Ile Gln Arg Leu Gly Cys Pro Glu Arg Leu Ala Ser
                2885            2890
```

SYNTHETIC ANTIGENS FOR THE DETECTION OF ANTIBODIES TO HEPATITIS C VIRUS

This application is a continuation of application Ser. No. 07/920,286, filed Oct. 14, 1992 abandoned, which is a 371 of PCT/EP91/02409, filed Dec. 31, 1991.

The implementation of systematic testing for hepatitis B virus (HBV) has been instrumental in eliminating this virus from the blood supply. Nevertheless, a significant number of post-transfusion hepatitis (PTH) cases still occur. These cases are generally attributable to non-A, non-B hepatitis (NANBH) virus(es), the diagnosis of which is usually made by exclusion of other viral markers.

The etiological agent responsible for a large proportion of these cases has recently been cloned (Choo, Q-L et al. Science (1988) 244:359–362) and a first-generation antibody test developed (Kuo, G. et al. Science (1989) 244:362–364). The agent has been identified as a positive-stranded RNA virus, and the sequence of its genome has been partially determined. Studies suggest that this virus, referred to subsequently as hepatitis C virus (HCV), may be related to flaviviruses and pestiviruses. A portion of the genome of an HCV isolated from a chimpanzee ($HCV_{CDC/CHI}$) is disclosed in EPO 88310922.5. The coding sequences disclosed in this document do not include sequences originating from the 5'-end of the viral genome which code for putative structural proteins. Recently however, sequences derived from this region of the HCV genome have been published (Okamoto, H. et al., Japan J. Exp. Med. 60:167–177, 1990.). The amino acid sequences encoded by the Japanese clone HC-J1 were combined with the $HCV_{CDC/CHI}$ sequences in a region where the two sequences overlap to generate the composite sequence depicted in FIG. 1. Specifically, the two sequences were joined at glycine$_{45}$. It should be emphasized that the numbering system used for the HCV amino acid sequence is not intended to be absolute since the existence of variant HCV strains harboring deletions or insertions is highly probable. Sequences corresponding to the 5' end of the HCV genome have also recently been disclosed in EPO 90302866.0.

In order to detect potential carriers of HCV, it is necessary to have access to large amounts of viral proteins. In the case of HCV, there is currently no known method for culturing the virus, which precludes the use of virus-infected cultures as a source of viral antigens. The current first-generation antibody test makes use of a fusion protein containing a sequence of 363 amino acids encoded by the HCV genome. It was found that antibodies to this protein could be detected in 75 to 85% of chronic NANBH patients. In contrast, only approximately 15% of those patients who were in the acute phase of the disease, had antibodies which recognized this fusion protein (Kuo, G. et al. Science (1989) 244:362–364). The absence of suitable confirmatory tests, however, makes it difficult to verify these statistics. The seeming similarity between the HCV genome and that of flaviviruses makes it possible to predict the location of epitopes which are likely to be of diagnostic value. An analysis of the HCV genome reveals the presence of a continuous long open reading frame. Viral RNA is presumably translated into a long polyprotein which is subsequently cleaved by cellular and/or viral proteases. By analogy with, for example, Dengue virus, the viral structural proteins are presumed to be derived from the amino-terminal third of the viral polyprotein. At the present time, the precise sites at which the polyprotein is cleaved can only be surmised. Nevertheless, the structural proteins are likely to contain epitopes which would be useful for diagnostic purposes, both for the detection of antibodies as well as for raising antibodies which could subsequently be used for the detection of viral antigens. Similarly, domains of nonstructural proteins are also expected to contain epitopes of diagnostic value, even though these proteins are not found as structural components of virus particles.

BRIEF DESCRIPTION OF THE DRAWINGS

FIGS. 1A–1D shows the amino acid sequence of the composite $HCV_{HC-J1/CDC/CHI}$(SEQ ID NO:23)

FIGS. 2A–2L show the antibody binding to individual peptides and various mixtures in an ELISA assay. Coating combinations used for FIGS. 2A–2L are as follows:

Figure 2E:
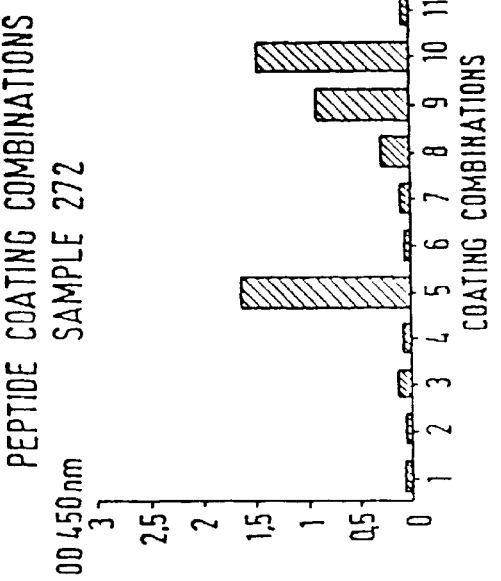

1:IX,2:XVIII, 3:1,4:III,5:V,6:IX+XVIII,7:I+XVIII,8:I+III+IX, 9:I+III+V+XVIII,10:I+III+V+IX,11:I+III+IX+XVIII,12:I+III+V+IX+XVIII.

DESCRIPTION OF THE SPECIFIC EMBODIMENTS

It is known that RNA viruses frequently exhibit a high rate of spontaneous mutation and, as such, it is to be expected that no two HCV isolates will be completely identical, even when derived from the same individual. For the purpose of this disclosure, a virus is considered to be the same or equivalent to HCV if it exhibits a global homology of 60 percent or more with the $HCV_{HC-J1/CDC/CHI}$ composite sequence at the nucleic acid level and 70 percent at the amino acid level.

Peptides are described which immunologically mimic proteins encoded by HCV. In order to accommodate strain-to-strain variations in sequence, conservative as well as non-conservative amino acid substitutions may be made. These will generally account for less than 35 percent of a specific sequence. It may be desirable in cases where a peptide corresponds to a region in the HCV polypeptide which is highly polymorphic, to vary one or more of the amino acids so as to better mimic the different epitopes of different viral strains.

The peptides of interest will include at least five, sometimes six, sometimes eight, sometimes twelve, usually fewer than about fifty, more usually fewer than about thirty-five, and preferably fewer than about twenty-five amino acids included within the sequence encoded by the HCV genome. In each instance, the peptide will preferably be as small as possible while still maintaining substantially all of the sensitivity of the larger peptide. It may also be desirable in certain instances to join two or more peptides together in one peptide structure.

It should be understood that the peptides described need not be identical to any particular HCV sequence, so long as the subject compounds are capable of providing for immunological competition with at least one strain of HCV. The peptides may therefore be subject to insertions, deletions, and conservative or non-conservative amino acid substitutions where such changes might provide for certain advantages in their use.

Substitutions which are considered conservative are those in which the chemical nature of the substitute is similar to that of the original amino acid. Combinations of amino acids which could be considered conservative are Gly, Ala; Asp, Glu; Asn, Gln; Val, Ile, Leu; Ser, Thr; Lys, Arg; and Phe, Tyr.

Furthermore, additional amino acids or chemical groups may be added to the amino- or carboxyl terminus for the purpose of creating a "linker arm" by which the peptide can conveniently be attached to a carrier. The linker arm will be at least one amino acid and may be as many as 60 amino acids but will most frequently be 1 to 10 amino acids. The nature of the attachment to a solid phase or carrier need not be covalent. Natural amino acids such as cysteine, lysine, tyrosine, glutamic acid, or aspartic acid may be added to either the amino- or carboxyl terminus to provide functional groups for coupling to a solid phase or a carrier. However, other chemical groups such as, for example, biotin and thioglycolic acid, may be added to the termini which will endow the peptides with desired chemical or physical properties. The termini of the peptides may also be modified, for example, by N-terminal acetylation or terminal carboxyamidation. The peptides of interest are described in relation to the composite amino acid sequence shown in FIG. 1. The amino acid sequences are given in the conventional and universally accepted three-letter code. In addition to the amino acids shown, other groups are defined as follows: Y is, for example, $NH_2$, one or more N-terminal amino acids, or other moieties added to facilitate coupling. Y may itself be modified by, for example, acetylation. Z is a bond, (an) amino acid(s), or (a) chemical group(s) which may be used for linking. X is intended to represent OH, $NH_2$, or a linkage involving either of these two groups.

Peptide I, shown in SEQ ID NO:1 corresponds to amino acids 1 to 20 and has the amino acid sequence:
(I)
Y-Met-Ser-Thr-Ile-Pro-Lys-Pro-Gln-Arg-Lys-Thr-Lys-Arg-Asn-Thr-Asn-Arg-Arg-Pro-Gln-Z-X.

Peptide II, shown in SEQ ID NO:2 corresponds to amino acids 7 to 26 and has the amino acid sequence:
(II)
Y-Pro-Gln-Arg-Lys-Thr-Lys-Arg-Asn-Thr-Asn-Arg-Arg-Pro-Gln-Asp-Val-Lys-Phe-Pro-Gly-Z-X.

Of particular interest is the oligopeptide IIA, shown in SEQ ID NO:3, which has the sequence:
(IIA)
Y-Gln-Arg-Lys-Thr-Lys-Arg-Asn-Thr-Asn-Arg-Arg-Z-X.

Peptide III, shown in SEQ ID NO:4 corresponds to amino acids 13 to 32 and has the sequence:
(III)
Y-Arg-Asn-Thr-Asn-Arg-Arg-Pro-Gln-Asp-Val-Lys-Phe-Pro-Gly-Gly-Gly-Gln-Ile-Val-Gly-Z-X.

Peptide IV, shown in SEQ ID NO:5 corresponds to amino acid 37 to 56 and has the sequence:
(IV)
Y-Leu-Pro-Arg-Arg-Gly-Pro-Arg-Leu-Gly-Val-Arg-Ala-Thr-Arg-Lys-Thr-Ser-Glu-Arg-Ser-Z-X.

Peptide V, shown in SEQ ID NO:6 corresponds to amino acids 49 to 68 and has the sequence:
(V)
Y-Thr-Arg-Lys-Thr-Ser-Glu-Arg-Ser-Gln-Pro-Arg-Gly-Arg-Arg-Gln-Pro-Ile-Pro-Lys-Val-Z-X.

Peptide VI, shown in SEQ ID NO:7, corresponds to amino acid 61 to 80 and has the following sequence:
(VI)
Y-Arg-Arg-Gln-Pro-Ile-Pro-Lys-Val-Arg-Arg-Pro-Glu-Gly-Arg-Thr-Trp-Ala-Gln-Pro-Gly-Z-X.

Peptide VII, shown in SEQ ID NO:8 corresponds to amino acids 73 to 92 and has the sequence:
(VII)
Y-Gly-Arg-Thr-Trp-Ala-Gln-Pro-Gly-Tyr-Pro-Trp-Pro-Leu-Tyr-Gly-Asn-Glu-Gly-Cys-Gly-Z-X.

Peptide VIII, shown in SEQ ID NO:9 corresponds to amino acids 1688 to 1707 and has the sequence:
(VIII)
Y-Leu-Ser-Gly-Lys-Pro-Ala-Ile-Ile-Pro-Asp-Arg-Glu-Val-Leu-Tyr-Arg-Glu-Phe-Asp-Glu-Z-X.

Peptide IX, shown in SEQ ID NO:10 corresponds to amino acids 1694 to 1713 and has the sequence:
(IX)
Y-Ile-Ile-Pro-Asp-Arg-Glu-Val-Leu-Tyr-Arg-Glu-Phe-Asp-Glu-Met-Glu-Glu-Cys-Ser-Gln-Z-X.

Peptide X, shown in SEQ ID NO:11 corresponds to amino acids 1706 to 1725 and has the sequence:
(X)
Y-Asp-Glu-Met-Glu-Glu-Cys-Ser-Gln-His-Leu-Pro-Tyr-Ile-Glu-Gln-Gly-Met-Met-Leu-Ala-Z-X.

Peptide XI, shown in SEQ ID NO:12 corresponds to amino acids 1712 to 1731 and has the sequence:
(XI)
Y-Ser-Gln-His-Leu-Pro-Tyr-Ile-Glu-Gln-Gly-Met-Met-Leu-Ala-Glu-Gln-Phe-Lys-Gln-Lys-Z-X.

Peptide XII, shown in SEQ ID NO:13 corresponds to amino acids 1718 to 1737 and has the sequence:
(XII)
Y-Ile-Glu-Gln-Gly-Met-Met-Leu-Ala-Glu-Gln-Phe-Lys-Gln-Lys-Ala-Leu-Gly-Leu-Leu-Gln-Z-X.

Peptide XIII, shown in SEQ ID NO:14 corresponds to amino acids 1724 to 1743 and has the sequence:
(XIII)
Y-Leu-Ala-Glu-Gln-Phe-Lys-Gln-Lys-Ala-Leu-Gly-Leu-Leu-Gln-Thr-Ala-Ser-Arg-Gln-Ala-Z-X.

Peptide XIV, shown in SEQ ID NO:15 corresponds to amino acids 1730 to 1749 and has the sequence:
(XIV)
Y-Gln-Lys-Ala-Leu-Gly-Leu-Leu-Gln-Thr-Ala-Ser-Arg-Gln-Ala-Glu-Val-Ile-Ala-Pro-Ala-Z-X.

Peptide XV, shown in SEQ ID NO:16 corresponds to amino acids 2263 to 2282 and has the sequence:
(XV)
Y-Glu-Asp-Glu-Arg-Glu-Ile-Ser-Val-Pro-Ala-Glu-Ile-Leu-Arg-Lys-Ser-Arg-Arg-Phe-Ala-Z-X.

Peptide XVI, shown in SEQ ID NO:17 corresponds to amino acids 2275 to 2294 and has the sequence:
(XVI)
Y-Leu-Arg-Lys-Ser-Arg-Arg-Phe-Ala-Gln-Ala-Leu-Pro-Val-Trp-Ala-Arg-Pro-Asp-Tyr-Asn-Z-X Peptide XVII, shown in SEQ ID NO:18 corresponds to amino acids 2287 to 2306 and has the sequence:
(XVII)
Y-Val-Trp-Ala-Arg-Pro-Asp-Tyr-Asn-Pro-Pro-Leu-Val-Glu-Thr-Trp-Lys-Lys-Pro-Asp-Tyr-Z-X.

Peptide XVIII, shown in SEQ ID NO:19 corresponds to amino acids 2299 to 2318 and has the sequence:
(XVIII)
Y-Glu-Thr-Trp-Lys-Lys-Pro-Asp-Tyr-Glu-Pro-Pro-Val-Val-His-Gly-Cys-Pro-Leu-Pro-Pro-Z-X.

Peptide XIX, shown in SEQ ID NO:20 corresponds to amino acids 2311 to 2330 and has the sequence:
(XIX)
Y-Val-His-Gly-Cys-Pro-Leu-Pro-Pro-Pro-Lys-Ser-Pro-Pro-Val-Pro-Pro-Pro-Arg-Lys-Lys-Z-X.

Of particular interest is the use of the mercapto-group of cysteines or thioglycolic acids used for acylating terminal amino groups for cyclizing the peptides or coupling two peptides together. The cyclization or coupling may occur via a single bond or may be accomplished using thiol-specific reagents to form a molecular bridge.

The peptides may be coupled to a soluble carrier for the purpose of either raising antibodies or facilitating the adsorption of the peptides to a solid phase. The nature of the carrier should be such that it has a molecular weight greater than 5000 and should not be recognized by antibodies in human serum. Generally, the carrier will be a protein.

Proteins which are frequently used as carriers are keyhole limpet hemocyanin, bovine gamma globulin, bovine serum albumin, and poly-L-lysine.

There are many well described techniques for coupling peptides to carriers. The linkage may occur at the N-terminus, C-terminus or at an internal site in the peptide. The peptide may also be derivatized for coupling. Detailed descriptions of a wide variety of coupling procedures are given, for example, in Van Regenmortel, M. H. V., Briand, J. P., Muller, S., and Plaué, S., Laboratory Techniques in Biochemistry and Molecular Biology, Vol. 19, Synthetic Polypeptides as Antigens, Elsevier Press, Amsterdarn, N.Y., Oxford, 1988.

The peptides may also be synthesized directly on an oligo-lysine core in which both the alpha as well as the epsilon-amino groups of lysines are used as growth points for the peptides. The number of lysines comprising the core is preferably 3 or 7. Additionally, a cysteine may be included near or at the C-terminus of the complex to facilitate the formation of homo- or heterodimers. The use of this technique has been amply illustrated for hepatitis B antigens (Tam, J. P., and Lu, Y-A., Proc. Natl. Acad. Sci. USA (1989) 86:9084–9088) as well as for a variety of other antigens (see Tam, J. P., Multiple Antigen Peptide System: A Novel Design for Synthetic Peptide Vaccine and Immunoassay, in Synthetic Peptides, Approaches to Biological Problems, Tar, J. P., and Kaiser, E. T., ed. Alan R. Liss Inc., New York, 1989).

Depending on their intended use, the peptides may be either labeled or unlabeled. Labels which may be employed may be of any type, such as enzymatic, chemical, fluorescent, luminescent, or radioactive. In addition, the peptides may be modified for binding to surfaces or solid phases, such as, for example, microtiter plates, nylon membranes, glass or plastic beads, and chromatographic supports such as cellulose, silica, or agarose. The methods by which peptides can be attached or bound to solid support or surface are well known to those versed in the art.

Of particular interest is the use of mixtures of peptides for the detection of antibodies specific for hepatitis C virus. Mixtures of peptides which are considered particularly advantageous are:

A. II, III, V, IX, and XVIII
B. I, II, V, IX XI, XVI, and XVIII
C. II, III, IV, V, VIII, XI, XVI, and XVIII
D. II, IX, and XVIII
E. II, III, IV, and V
F. VIII, IX, XI, XIII, and XIV
G. XV, XVI, XVII, XVIII, and XIX Antibodies which recognize the peptides can be detected in a variety of ways. A preferred method of detection is the enzyme-linked immunosorbant assay (ELISA) in which a peptide or mixture of peptides is bound to a solid support. In most cases, this will be a microtiter plate but may in principle be any sort of insoluble solid phase. A suitable dilution or dilutions of serum or other body fluid to be tested is brought into contact with the solid phase to which the peptide is bound. The incubation is carried out for a time necessary to allow the binding reaction to occur. Subsequently, unbound components are removed by washing the solid phase. The detection of immune complexes is achieved using antibodies which specifically bind to human immunoglobulins, and which have been labeled with an enzyme, preferably but not limited to either horseradish peroxidase, alkaline phosphatase, or beta-galactosidase, which is capable of converting a colorless or nearly colorless substrate or co-substrate into a highly colored product or a product capable of forming a colored complex with a chromogen. Alternatively, the detection system may employ an enzyme which, in the presence of the proper substrate(s), emits light. The amount of product formed is detected either visually, spectrophotometrically, electrochemically, or luminometrically, and is compared to a similarly treated control. The detection system may also employ radioactively labeled antibodies, in which case the amount of immune complex is quantified by scintillation counting or gamma counting.

Other detection systems which may be used include those based on the use of protein A derived from *Staphylococcus aureus* Cowan strain I, protein G from group C Staphylococcus sp. (strain 26RP66), or systems which make use of the high affinity biotin-avidin or streptavidin binding reaction.

Antibodies raised to carrier-bound peptides can also be used in conjunction with labeled peptides for the detection of antibodies present in serum or other body fluids by competition assay. In this case, antibodies raised to carrier-bound peptides are attached to a solid support which may be, for example, a plastic bead or a plastic tube. Labeled peptide is then mixed with suitable dilutions of the fluid to be tested and this mixture is subsequently brought into contact with the antibody bound to the solid support. After a suitable incubation period, the solid support is washed and the amount of labeled peptide is quantified. A reduction in the amount of label bound to the solid support is indicative of the presence of antibodies in the original sample. By the same token, the peptide may also be bound to the solid support. Labeled antibody may then be allowed to compete with antibody present in the sample under conditions in which the amount of peptide is limiting. As in the previous example, a reduction in the measured signal is indicative of the presence of antibodies in the sample tested.

Another preferred method of antibody detection is the homogeneous immunoassay. There are many possible variations in the design of such assays. By way of example, numerous possible configurations for homogeneous enzyme immunoassays and methods by which they may be performed are given in Tijssen, P., Practice and Theory of Enzyme Immunoassays, Elsevier Press, Amersham, Oxford, N.Y., 1985. Detection systems which may be employed include those based on enzyme channeling, bioluminescence, allosteric activation and allosteric inhibition. Methods employing liposome-entrapped enzymes or coenzymes may also be used (see Pinnaduwage, P. and Huang, L., *Clin. Chem.* (1988) 34/2: 268–272, and Ullman, E. F. et al., *Clin. Chem.* (1987) 33/9: 1579–1584 for examples).

The synthesis of the peptides can be achieved in solution or on a solid support. Synthesis protocols generally employ the use t-butyloxycarbonyl- or 9-fluorenylmethoxycarbonyl-protected activated amino acids. The procedures for carrying out the syntheses, the types of side-chain protection, and the cleavage methods are amply described in, for example, Stewart and Young, Solid Phase Peptide Synthesis, 2nd Edition, Pierce Chemical Company, 1984; and Atherton and Sheppard, Solid Phase Peptide Synthesis, IRL Press, 1989.

Experimental

I. Peptide Synthesis

All of the peptides described were synthesized on Pepsyn K polyamide-Kieselguhr resin (Milligen, Novato, Calif.) which had been functionalized with ethylenediamine and onto which the acid-labile linker 4-(alpha-Fmoc-amino-2', 4'-dimethoxybenzyl) phenoxyacetic acid had been coupled (Rink, Tetrahedron Lett. (1987) 28:3787). t-Butyl-based side-chain protection and Fmoc alpha-amino-protection was used. The guanidino-group of arginine was protected by the 2,2,5,7,8-pentamethylchroman-6-sulfonyl moiety. The imidazole group of histidine was protected by either t-Boc or trityl and the sulfhydryl group of cysteine was protected by a trityl group. Couplings were carried out using performed O-pentafluorophenyl esters except in the case of arginine where diisopropylcarbodiimide-mediated hydroxybenzotriazole ester formation was employed. Except for peptide I, all peptides were N-acetylated using acetic anhydride. All syntheses were carried out on a Milligen 9050 PepSynthesizer (Novato, Calif.) using continuous flow procedures. Following cleavage with trifluoroacetic acid in the presence of scavengers and extraction with diethylether, all peptides were analyzed by $C_{18}$-reverse phase chromatography.

II. Detection of Antibodies to Hepatitis C Virus

A. Use of Peptides Bound to a Nylon Membrane.

Peptides were dissolved in a suitable buffer to make a concentrated stock solution which was then further diluted in phosphate-buffered saline (PBS) or sodium carbonate buffer, pH 9.6 to make working solutions. The peptides were applied as lines on a nylon membrane (Pall, Portsmouth, United Kingdom), after which the membrane was treated with casein to block unoccupied binding sites. The membrane was subsequently cut into strips perpendicular to the direction of the peptide lines. Each strip was then incubated with a serum sample diluted 1 to 100, obtained from an HCV-infected individual. Antibody binding was detected by incubating the strips with goat anti-human immunoglobulin antibodies conjugated to the enzyme alkaline phosphatase. After removing unbound conjugate by washing, a substrate solution containing 5-bromo-4-chloro-3-indolylphosphate and nitro blue tetrazolium was added.

Positive reactions are visible as colored lines corresponding to the positions of the peptides which are specifically recognized. The reaction patterns of thirty-six different sera are tabulated in Table 1. The results shown in Table 1 are further summarized in Table 2.

B. Use of Peptides in an Enzyme-linked Immunosorbent Assay (ELISA).

Peptide stock solutions were diluted in sodium carbonate buffer, pH 9.6 and used to coat microtiter plates at a peptide concentration of 2 micrograms per milliliter. A mixture consisting of peptides II, III, V, IX, and XVIII was also used to coat plates. Following coating, the plates were blocked with casein. Fifteen HCV-antibody-positive sera and control sera from seven uninfected blood donors were diluted 1 to 20 and incubated in wells of the peptide-coated plates. Antibody binding was detected by incubating the plates with goat anti-human immunoglobulin antibodies conjugated to the enzyme horseradish peroxidase. Following removal of unbound conjugate by washing, a solution containing $H_2O_2$ and 3,3',5,5'-tetramethylbenzidine was added. Reactions were stopped after a suitable interval by addition of sulfuric acid. Positive reactions gave rise to a yellow color which was quantified using a conventional microtiter plate reader. The results of these determinations are tabulated in Table 3. To correct for any aspecific binding which could be attributable to the physical or chemical properties of the peptides themselves, a cut-off value was determined for each peptide individually. This cut-off absorbance value was calculated as the average optical density of the negative samples plus 0.200. Samples giving absorbance values higher than the cut-off values are considered positive. The results for the fifteen positive serum samples are further summarized in Table 4.

While it is evident that some of the peptides are recognized by a large percentage of sera from HCV-infected individuals, it is also clear that no single peptide is recognized by all sera. In contrast, the peptide mixture was recognized by all fifteen sera and, for six of the fifteen sera, the optical densities obtained were equal to or higher than those obtained for any of the peptides individually. These results serve to illustrate the advantages of using mixtures of peptides for the detection of anti-HCV antibodies.

C. Binding of Antibodies in Sera from HCV-infected Patients to Various Individual Peptides and Peptide Mixtures in an ELISA.

Figure 2D:
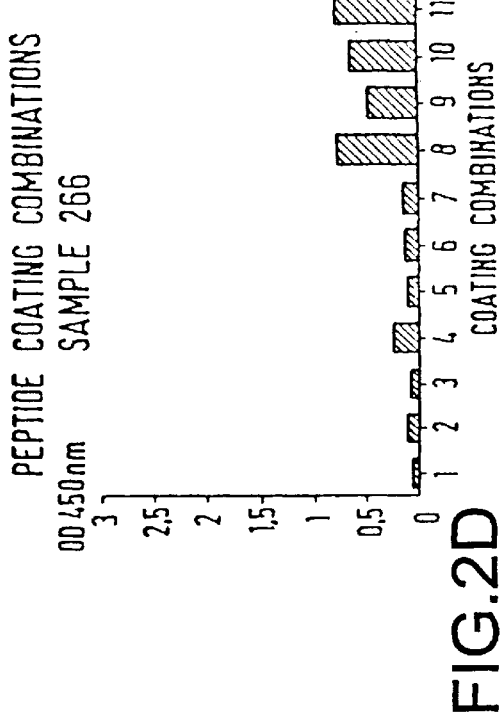
Figure 2F:
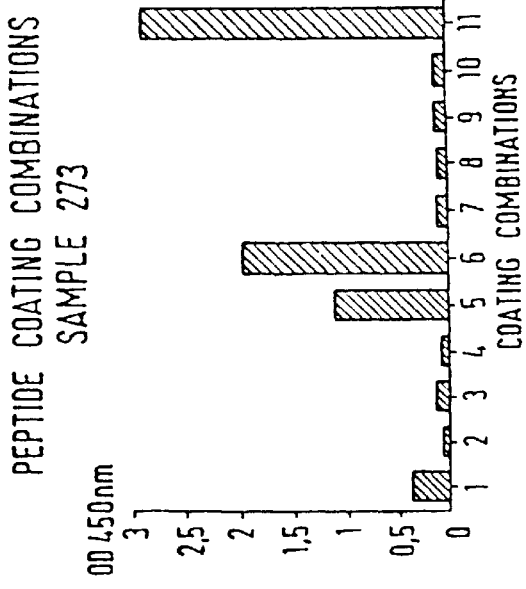
Figures 2G, 2H, 2I:

Five peptides were used individually and in seven different combinations to coat microtiter plates. The plates were subsequently incubated with dilutions of fifteen HCV antibody-positive sera in order to evaluate the relative merits of using mixtures as compared to individual peptides for antibody detection. The mixtures used and the results obtained are shown in FIG. 2.

In general, the mixtures functioned better than individual peptides. This was particularly evident for mixture 12 (peptides I, III, V, IX, and XVIII) which was recognized by all twelve of the sera tested. These results underscore the advantages of using mixtures of peptides in diagnostic tests for the detection of antibodies to HCV.

D. Use of a Mixture of Peptides in an ELISA Assay for the Detection of Anti-HCV Antibodies.

A mixture of peptides II, III, V, IX and XVIII was prepared and used to coat microtiter plates according to the same procedure used to test the individual peptides. A total of forty-nine sera were tested from patients with clinically diagnosed but undifferentiated chronic non A non B hepatitis as well as forty-nine sera from healthy blood donors. Detection of antibody binding was accomplished using goat anti-human immunoglobulin antibodies conjugated to horseradish peroxidase. The resulting optical density values are given in Table 5. These results indicate that the mixture of peptides is not recognized by antibodies in sera from healthy donors (0/49 reactives) but is recognized by a large proportion (41/49, or 84%) of the sera from patients with chronic NANBH. These results demonstrate that the peptides described can be used effectively as mixtures for the diagnosis of HCV infection.

E. Detection of Anti-HCV antibodies In Sera From Patients With Acute NANB Infection Using Individual Peptides Bound to Nylon Membranes and a Mixture of Peptides in an ELISA Assay, and Comparison With a Commercially Available Kit.

Peptides were applied to nylon membranes or mixed and used to coat microtiter plates as previously described. The peptide mixture consisted of peptides II, III, V, IX and XVIII. Sera obtained from twenty-nine patients with acute non-A, non-B hepatitis were then tested for the presence of antibodies to hepatitis C virus. These same sera were also evaluated using a commercially available kit (Ortho, Emeryville, Calif., USA).

The results of this comparative study are given in Table 6. In order to be able to compare the peptide-based ELISA with the commercially available kit, the results for both tests are also expressed as signal to noise ratios (S/N) which were calculated by dividing the measured optical density obtained for each sample by the cut-off value. A signal-to-noise ratio greater or equal to 1.0 is taken to represent a positive reaction. For the commercially available kit, the cut-off value was calculated according to the manufacturer's instructions. The cut-off value for the peptide-based ELISA was calculated as the average optical density of five negative samples plus 0.200.

The scale used to evaluate antibody recognition of nylon-bound peptides was the same as that given in Table 1. Of the twenty-nine samples tested, twenty-five (86%) were positive in the peptide-based ELISA and recognized one or more nylon-bound peptides. In contrast, only fourteen of the twenty-nine sera scored positive in the commercially available ELISA These results serve to illustrate the advantages of using peptide mixtures for the detection of anti-HIV antibodies as well as the need to include in the mixtures peptides which contain amino acid sequences derived from different regions of the HCV polyprotein.

TABLE 1

Recognition of peptides bound to nylon membranes by sera from persons infected by HCV.

| Serum nr. | I | II | III | IV | V | VI | VII | VIII | IX | X | XI | XII | XIII | XIV | XV | XVI | XVII | XVIII | XIX |
|---|---|---|---|---|---|---|---|---|---|---|---|---|---|---|---|---|---|---|---|
| 1 | | | 3 | 1 | | | | 1 | | | 0.5 | | | | | 2 | 2 | 1 | 1 |
| 2 | | | | | | | | | | | 0.5 | | 1 | 2 | | 2 | 1 | | |
| 3 | 1 | 0.5 | 2 | 1 | | 0.5 | | 2 | 0.5 | 1 | 0.5 | | | | | | | | |
| 4 | | | | | | | | | | | | | 1 | | | | | | |
| 6 | | | 2 | 1 | 0.5 | | | | | | | | | | | 2 | | | |
| 7 | 0.5 | 1 | 2 | 1 | 0.5 | | | 3 | 2 | 2 | 1 | | 1 | | 2 | | 0.5 | 1 | 1 |
| 8 | 0.5 | 1 | 3 | 1 | 1 | | 1 | 1 | | 2 | 1 | | 1 | | | 1 | 1 | 0.5 | |
| 10 | | 1 | 0.5 | | | | | 3 | 1 | 1 | | | | 0.5 | 2 | 2 | | 2 | 2 |
| 13 | 0.5 | 0.5 | 2 | | 0.5 | | | | | 1 | | | 1 | 0.5 | | 0.5 | | | |
| 15 | | | | 0.5 | | | | 2 | 1 | 0.5 | | | | 1 | | 0.5 | | | |
| 16 | 2 | 1 | 0.5 | 0.5 | 1 | 0.5 | | 2 | 0.5 | 1 | | | | | 2 | 2 | 1 | 2 | |
| 18 | 1 | 1 | 3 | 0.5 | | 2 | 0.5 | | | | | | | | | 1 | 0.5 | | |
| 23 | 0.5 | | 1 | 1 | | | 0.5 | | | 1 | 0.5 | | 0.5 | | 0.5 | | | | |
| 24 | 1 | 0.5 | 2 | 1 | 0.5 | 0.5 | 0.5 | 2 | | | | | | | | 1 | | | |
| 25 | | 1 | 0.5 | | | | | 2 | 0.5 | 0.5 | 2 | | 1 | 1 | | 2 | | | |
| 26 | | | | | | | | 1 | | | | | | | | 0.5 | | | |
| 27 | 0.5 | 0.5 | 1 | | | | | 3 | 2 | | | | | | | 1 | 2 | 1 | 0.5 |
| 29 | | 0.5 | 3 | 2 | 1 | 1 | 0.5 | | 2 | 1 | | | 1 | 1 | 2 | 2 | 1 | 1 | 1 |
| 30 | | 0.5 | 0.5 | 1 | 1 | 0.5 | | | | | | | | | | | | | |
| 31 | | 1 | 0.5 | | | | | | | 0.5 | 0.5 | | | | 0.5 | | | | |
| 32 | | 1 | 2 | | | | | | | 1 | 0.5 | | | 1 | 1 | | | | |
| 33 | | | | | | | | 0.5 | | 1 | 0.5 | | | | | | | 0.5 | |
| 34 | | 1 | 1 | 1 | | | | 3 | 1 | | | | | | | 1 | 1 | 0.5 | |
| 35 | 1 | 1 | 2 | 1 | 1 | 1 | 0.5 | | | | | | | | | | | | |
| 36 | 1 | | 2 | 1 | | 1 | | | | | | | | | | | | | |
| 37 | 1 | 1 | | | | | | | | | | | | | | | | | |
| 44 | | 1 | 2 | 1 | 0.5 | | | | | | | | | | 2 | | 0.5 | | |
| 46 | | 0.5 | 2 | 0.5 | 0.5 | | 0.5 | 2 | | | | | | | | | | | |
| 47 | | 0.5 | | 0.5 | | 0.5 | | 1 | | | | | | | | | | 1 | 1 |
| 48 | 1 | 2 | | 2 | | | 0.5 | 2 | | | | | 0.5 | | 1 | 1 | | 1 | 0.5 |
| 49 | | 1 | 1 | 0.5 | 0.5 | 0.5 | | | | 0.5 | 0.5 | | 0.5 | | | | 1 | | |
| 50 | | 1 | 2 | 1 | | | | 2 | 0.5 | 1 | 1 | | 1 | | | 1 | 1 | 0.5 | 0.5 |
| 51 | | | 2 | 0.5 | 0.5 | | 0.5 | | | | | | | | | 1 | 1 | 0.5 | |
| 52 | | | 2 | 0.5 | | | 0.5 | | | 0.5 | | | | | | | | | |
| 54 | | | 2 | 0.5 | 0.5 | 1 | 0.5 | | | 1 | | 1 | | 2 | | 1 | 1 | 1 | |
| 56 | ND | ND | ND | ND | ND | ND | ND | 2 | | | 0.5 | 1 | 2 | 1 | | | | | |

Blank: no reation; 0.5: weakly positive; 1: clearly positive; 2: strong reaction; 3: intense reaction; ND: not determined

TABLE 2

Summary of antibody binding to nylon-bound HCV peptides by sera from infected patients.

| Peptide | No. reactive sera | % reactive sera |
|---|---|---|
| I | 13/35 | 37 |
| II | 22/35 | 63 |
| III | 27/35 | 77 |
| IV | 24/35 | 69 |
| V | 14/35 | 40 |
| VI | 11/35 | 31 |
| VII | 11/35 | 31 |
| VIII | 19/36 | 53 |
| IX | 9/36 | 25 |
| X | 17/36 | 47 |
| XI | 15/36 | 42 |
| XII | 1/36 | 3 |
| XIII | 13/36 | 36 |
| XIV | 7/36 | 19 |
| XV | 9/36 | 25 |
| XVI | 20/36 | 56 |
| XVII | 14/36 | 39 |
| XVIII | 14/36 | 39 |
| XIX | 8/36 | 22 |

TABLE 3

Comparison of Individual Peptides in an ELISA Assay for the Detection of Antibodies to HCV.

| sample ident | I | II | III | IV | V | VI | VII | VIII | IX | X | XI | XII | XIII | XIV | XV | XVI | XVII | XVIII | XIX |
|---|---|---|---|---|---|---|---|---|---|---|---|---|---|---|---|---|---|---|---|
| 1 | 0.786 | 1.119 | 1.284 | 0.265 | 0.042 | 0.04 | 0.05 | 0.571 | 0.659 | 0.048 | 0.04 | 0.043 | 0.068 | 0.044 | 0.041 | 1.063 | 0.956 | 1.383 | 1.346 |
| 2 | 0.044 | 0.039 | 0.11 | 0.041 | 0.037 | 0.038 | 0.039 | 0.479 | 0.78 | 0.169 | 0.563 | 0.039 | 0.042 | 0.515 | 0.039 | 0.64 | 0.319 | 0.154 | 0.49 |
| 3 | 0.815 | 0.944 | 0.825 | 0.399 | 0.654 | 0.487 | 0.32 | 0.705 | 0.965 | 0.468 | 0.668 | 0.041 | 0.093 | 0.341 | 0.043 | 0.292 | 0.038 | 0.046 | 0.038 |
| 7 | 1.122 | 1.23 | 0.588 | 0.682 | 0.659 | 0.182 | 0.107 | 0.907 | 1.42 | 0.663 | 0.646 | 0.041 | 0.235 | 0.068 | 0.575 | 0.042 | 0.041 | 0.872 | 1.271 |
| 8 | 1.155 | 1.159 | 1.2 | 0.508 | 1.272 | 0.433 | 0.623 | 0.61 | 0.863 | 0.752 | 1.175 | 0.046 | 0.42 | 0.102 | 0.068 | 0.552 | 0.671 | 0.417 | 0.058 |
| 10 | 1.089 | 1.236 | 1.083 | 0.044 | 0.508 | 0.042 | 0.073 | 1.49 | 1.529 | 0.689 | 0.834 | 0.041 | 0.044 | 0.314 | 0.793 | 0.886 | 0.037 | 1.335 | 1.356 |
| 11 | 0.048 | 0.051 | 0.476 | 0.052 | 0.119 | 0.039 | 0.1 | 0.634 | 0.711 | 0.199 | 0.967 | 0.125 | 0.454 | 0.088 | 0.111 | 0.274 | 0.093 | 0.838 | 0.065 |
| 15 | 0.224 | 0.602 | 0.813 | 0.093 | 0.068 | 0.077 | 0.147 | 0.807 | 1.225 | 0.315 | 0.688 | 0.046 | 0.154 | 0.202 | 0.065 | 0.372 | 0.097 | 0.155 | 0.077 |
| 23 | 0.62 | 0.8 | 0.924 | 0.568 | 0.759 | 0.442 | 0.683 | 0.089 | 0.121 | 0.422 | 0.896 | 0.041 | 0.049 | 0.101 | 0.068 | 0.311 | 0.038 | 0.052 | 0.05 |
| 24 | 1.042 | 1.132 | 1.026 | 0.518 | 0.916 | 0.302 | 0.253 | 1.013 | 1.364 | 0.236 | 0.397 | 0.054 | 0.123 | 0.076 | 0.051 | 0.418 | 0.053 | 0.1 | 0.085 |
| 49 | 0.624 | 0.73 | 0.884 | 0.171 | 0.372 | 0.055 | 0.04 | 0.084 | 0.064 | 0.209 | 0.731 | 0.044 | 0.113 | 0.039 | 0.044 | 0.299 | 0.038 | 0.192 | 0.041 |
| 13 | 0.76 | 0.857 | 0.815 | 0.087 | 0.422 | 0.098 | 0.045 | 0.473 | 0.489 | 0.529 | 0.735 | 0.043 | 0.044 | 0.186 | 0.043 | 0.086 | 0.037 | 0.066 | 0.04 |
| 31 | 0.84 | 1.114 | 0.445 | 0.672 | 0.046 | 0.041 | 0.042 | 0.184 | 0.15 | 0.255 | 0.69 | 0.041 | 0.04 | 0.061 | 0.136 | 0.292 | 0.038 | 0.224 | 0.501 |
| 47 | 1.303 | 1.53 | 1.236 | 0.751 | 0.83 | 0.629 | 0.073 | 0.545 | 0.739 | 0.044 | 0.041 | 0.041 | 0.041 | 0.498 | 0.04 | 0.268 | 0.042 | 1.288 | 1.206 |
| 56 | 1.169 | 1.301 | 1.364 | 1.269 | 1.374 | 0.85 | 1.066 | 1.45 | 1.523 | 0.079 | 1.069 | 0.058 | 0.568 | 0.038 | 0.039 | 0.218 | 0.036 | 0.087 | 0.039 |
| bd A28 | 0.054 | 0.043 | 0.139 | 0.045 | 0.135 | 0.042 | 0.041 | 0.086 | 0.115 | 0.044 | 0.042 | 0.044 | 0.052 | 0.043 | 0.043 | 0.307 | 0.042 | 0.045 | 0.061 |
| bd A169 | 0.041 | 0.042 | 0.134 | 0.044 | 0.038 | 0.04 | 0.041 | 0.061 | 0.07 | 0.043 | 0.042 | 0.041 | 0.04 | 0.041 | 0.041 | 0.255 | 0.038 | 0.056 | 0.042 |
| bd A170 | 0.04 | 0.044 | 0.117 | 0.04 | 0.036 | 0.04 | 0.04 | 0.081 | 0.05 | 0.04 | 0.039 | 0.04 | 0.038 | 0.038 | 0.144 | 0.292 | 0.036 | 0.058 | 0.039 |
| bd A171 | 0.041 | 0.046 | 0.148 | 0.043 | 0.037 | 0.045 | 0.045 | 0.077 | 0.065 | 0.043 | 0.041 | 0.043 | 0.039 | 0.04 | 0.045 | 0.286 | 0.037 | 0.05 | 0.04 |
| bd A166 | 0.047 | 0.046 | 0.124 | 0.044 | 0.038 | 0.042 | 0.041 | 0.056 | 0.066 | 0.041 | 0.041 | 0.042 | 0.04 | 0.041 | 0.041 | 0.207 | 0.039 | 0.046 | 0.041 |
| bd A165 | 0.041 | 0.046 | 0.123 | 0.043 | 0.035 | 0.051 | 0.042 | 0.051 | 0.091 | 0.041 | 0.04 | 0.042 | 0.039 | 0.043 | 0.039 | 0.253 | 0.034 | 0.06 | 0.098 |
| AVG | 0.044 | 0.045 | 0.131 | 0.043 | 0.053 | 0.043 | 0.042 | 0.069 | 0.076 | 0.042 | 0.041 | 0.042 | 0.041 | 0.041 | 0.059 | 0.267 | 0.038 | 0.053 | 0.054 |
| STD | 0.005 | 0.002 | 0.011 | 0.002 | 0.037 | 0.004 | 0.002 | 0.013 | 0.021 | 0.001 | 0.001 | 0.001 | 0.005 | 0.002 | 0.038 | 0.033 | 0.002 | 0.006 | 0.021 |
| cut off | 0.109 | 0.101 | 0.214 | 0.099 | 0.214 | 0.105 | 0.098 | 0.158 | 0.189 | 0.095 | 0.094 | 0.095 | 0.106 | 0.097 | 0.223 | 0.416 | 0.084 | 0.121 | 0.167 |

TABLE 4

Summary of antibody-binding to individual peptides in an ELISA assay.

| Peptide | No. reactive sera | % reactive sera |
|---|---|---|
| I | 13 | 87 |
| II | 13 | 87 |
| III | 14 | 93 |
| IV | 10 | 67 |
| V | 10 | 67 |
| VI | 7 | 47 |
| VII | 8 | 53 |
| VIII | 13 | 87 |
| IX | 12 | 80 |
| X | 13 | 87 |
| XI | 13 | 87 |
| XII | 1 | 7 |
| XIII | 7 | 47 |
| XIV | 8 | 53 |
| XV | 2 | 13 |
| XVI | 5 | 33 |
| XVII | 4 | 27 |
| XVIII | 10 | 67 |
| XIX | 6 | 40 |

TABLE 5

Use of a peptide mixture for the detection of antibodies to HCV in sera from chronic NANBH patients and comparison to sera from healthy blood donors.

| Chronic NANB Sera | | Control Sera | |
|---|---|---|---|
| Serum nr. | Optical Density | Serum nr. | Optical Density |
| 101 | 0.041 | 1 | 0.049 |
| 102 | 1.387 | 2 | 0.047 |
| 103 | 1.578 | 3 | 0.049 |
| 104 | 1.804 | 4 | 0.046 |
| 105 | 1.393 | 5 | 0.049 |
| 107 | 1.604 | 6 | 0.045 |
| 108 | 1.148 | 7 | 0.043 |
| 109 | 1.714 | 8 | 0.053 |
| 110 | 1.692 | 9 | 0.049 |
| 112 | 0.919 | 10 | 0.047 |
| 113 | 1.454 | 11 | 0.060 |
| 114 | 0.936 | 12 | 0.044 |
| 115 | 0.041 | 13 | 0.049 |
| 116 | 1.636 | 14 | 0.051 |
| 118 | 1.242 | 15 | 0.056 |
| 119 | 1.568 | 16 | 0.050 |
| 120 | 1.290 | 17 | 0.049 |
| 121 | 1.541 | 18 | 0.055 |
| 122 | 1.422 | 19 | 0.054 |
| 123 | 1.493 | 20 | 0.058 |
| 124 | 1.666 | 21 | 0.050 |
| 125 | 1.644 | 22 | 0.044 |
| 126 | 1.409 | 23 | 0.043 |
| 127 | 1.625 | 24 | 0.045 |
| 128 | 1.061 | 25 | 0.046 |
| 129 | 1.553 | 26 | 0.049 |
| 130 | 1.709 | 27 | 0.050 |
| 131 | 0.041 | 28 | 0.047 |
| 132 | 0.044 | 29 | 0.050 |
| 133 | 1.648 | 30 | 0.053 |
| 134 | 0.043 | 31 | 0.051 |
| 135 | 1.268 | 32 | 0.053 |
| 136 | 1.480 | 33 | 0.055 |
| 138 | 0.628 | 34 | 0.064 |
| 139 | 0.042 | 35 | 0.063 |
| 140 | 0.040 | 36 | 0.057 |
| 141 | 0.039 | 38 | 0.048 |
| 142 | 1.659 | 39 | 0.045 |
| 143 | 1.457 | 40 | 0.046 |

TABLE 5-continued

Use of a peptide mixture for the detection of antibodies to HCV in sera from chronic NANBH patients and comparison to sera from healthy blood donors.

| Chronic NANB Sera | | Control Sera | |
|---|---|---|---|
| Serum nr. | Optical Density | Serum nr. | Optical Density |
| 144 | 0.722 | 41 | 0.046 |
| 145 | 1.256 | 42 | 0.051 |
| 146 | 0.373 | 43 | 0.057 |
| 147 | 1.732 | 44 | 0.050 |
| 148 | 1.089 | 45 | 0.050 |
| 149 | 1.606 | 46 | 0.045 |
| 150 | 1.725 | 47 | 0.041 |
| 151 | 1.449 | 48 | 0.064 |
| 154 | 1.639 | 49 | 0.040 |
| 155 | 1.775 | 50 | 0.036 |

TABLE 6

Comparison of anti-HCV antibody detection by nylon bound peptides, a peptide based ELISA, and a commercially available kit.

| | Nylon-bound peptide | | | | | | | | | | | Optical density | | Optical density | |
|---|---|---|---|---|---|---|---|---|---|---|---|---|---|---|---|
| Serum nr. | I | III | IV | V | VI | VIII | XI | XIV | XV | XVI | XVIII | Peptide ELISA | S/N | Commercial ELISA | S/N |
| 191 | 0 | 0 | 0 | 0 | 0 | 0 | 0 | 0 | 0 | 0 | 0 | 0.045 | 0.18 | 0.295 | 0.47 |
| 192 | 0 | 0 | 0 | 0 | 0 | 0 | 0 | 0 | 0 | 0 | 0 | 0.042 | 0.17 | 0.289 | 0.46 |
| 193 | 0 | 0 | 0 | 0 | 0 | 0 | 0 | 0 | 0 | 0 | 0 | 0.039 | 0.16 | 0.197 | 0.32 |
| 194 | 0 | 0 | 0 | 0 | 0 | 0 | 0 | 0 | 0 | 0 | 0 | 0.044 | 0.18 | 0.183 | 0.29 |
| 195 | 1 | 2 | 2 | 3 | 0 | 0 | 0.5 | 0.5 | 1 | 3 | 1 | 1.692 | 6.77 | 3.000* | 4.82* |
| 196 | 1 | 2 | 1 | 2 | 0.5 | 0.5 | 0.5 | 0.5 | 0.5 | 2 | 0 | 1.569 | 6.28 | 0.386 | 0.62 |
| 197 | 1 | 2 | 1 | 2 | 0 | 0.5 | 0.5 | 0.5 | 1 | 2 | 0 | 1.523 | 6.09 | 0.447 | 0.72 |
| 198 | 1 | 2 | 2 | 2 | 0 | 0 | 0 | 0 | 1 | 2 | 0 | 1.578 | 6.31 | 0.354 | 0.57 |
| 211 | 0.5 | 1 | 0.5 | 0.5 | 0 | 2 | 2 | 0 | 2 | 0 | 1 | 1.606 | 6.42 | 3.000* | 4.82* |
| 213 | 0 | 0 | 0 | 1 | 0 | 0 | 0 | 0 | 0 | 0 | 0 | 0.369 | 1.48 | 0.127 | 0.20 |
| 214 | 0 | 0 | 0 | 1 | 0 | 0 | 0 | 0 | 0 | 0 | 0 | 0.444 | 1.78 | 0.101 | 0.16 |
| 215 | 0 | 0 | 0 | 1 | 0 | 0 | 0 | 0 | 0 | 0 | 0 | 0.637 | 2.55 | 0.101 | 0.16 |
| 216 | 0 | 0 | 0 | 0.5 | 0 | 0 | 0 | 0 | 0 | 0 | 0 | 0.812 | 3.25 | 0.092 | 0.15 |
| 217 | 0 | 0 | 0 | 1 | 0 | 0 | 0 | 0 | 0 | 0 | 0 | 1.320 | 5.28 | 0.875 | 1.40 |
| 219 | 0.5 | 1 | 1 | 2 | 1 | 0.5 | 1 | 0 | 0.5 | 0.5 | 1 | 1.547 | 6.19 | 3.000* | 4.82* |
| 220 | 0.5 | 1 | 1 | 2 | 1 | 0.5 | 1 | 0 | 0.5 | 0.5 | 1 | 1.536 | 6.14 | 3.000* | 4.82* |
| 221 | 0 | 0 | 0 | 0.5 | 0 | 0 | 0 | 0 | 0 | 0 | 0 | 1.428 | 5.71 | 0.327 | 0.52 |
| 222 | 1 | 1 | 1 | 1 | 0 | 0 | 2 | 0.5 | 0.5 | 0 | 0 | 1.362 | 5.45 | 3.000* | 4.82* |
| 223 | 1 | 1 | 1 | 1 | 0 | 0 | 3 | 0.5 | 0.5 | 0 | 0 | 1.316 | 5.26 | 3.000* | 4.82* |
| 224 | 1 | 1 | 2 | 1 | 0 | 0.5 | 3 | 0.5 | 0.5 | 0 | 0 | 1.304 | 5.22 | 3.000* | 4.82* |
| 225 | 0 | 0 | 0 | 0 | 0 | 0.5 | 0.5 | 0.5 | 0 | 0 | 2 | 1.178 | 4.71 | 2.398 | 3.85 |
| 226 | 0.5 | 0 | 0 | 0 | 0 | 2 | 3 | 2 | 0.5 | 0.5 | 3 | 1.256 | 5.14 | 3.000* | 4.82* |
| 227 | 0 | 0 | 0 | 0 | 0 | 2 | 2 | 0.5 | 0.5 | 0.5 | 2 | 1.335 | 5.34 | 3.000* | 4.82* |
| 228 | 0.5 | 0 | 0.5 | 0.5 | 0 | 2 | 2 | 2 | 0 | 0 | 2 | 1.400 | 5.60 | 3.000* | 4.82* |
| 234 | 0.5 | 0.5 | 0 | 0.5 | 0 | 0 | 3 | 1 | 3 | 1 | 3 | 1.481 | 5.92 | 3.000* | 4.82* |
| 235 | 0 | 0 | 0 | 0.5 | 0 | 0 | 0 | 0 | 0 | 0 | 0 | 0.351 | 1.40 | 0.257 | 0.41 |
| 236 | 0 | 0 | 0 | 0.5 | 0 | 0 | 0 | 0 | 0 | 0 | 0 | 0.475 | 1.90 | 0.245 | 0.39 |
| 237 | 0 | 0 | 0 | 1 | 0 | 0 | 0 | 0 | 0 | 0 | 0 | 1.134 | 4.54 | 0.351 | 0.56 |
| 238 | 0 | 0 | 0 | 1 | 0 | 1 | 1 | 0 | 0 | 0 | 0 | 1.096 | 4.38 | 1.074 | 1.72 |
| | | | | | | | | | | | | Cut-off: 0.250 | | Cut-off: 0.623 | |

0: no reaction; 0.5: weakly positive; 1: clearly positive; 2: strong reaction; 3: intense reaction;
*O.D. exceeded 3.000 and was out of range. The values given are therefore minimum values.

We claim:

1. A peptide having the amino acid sequence:
Glu-Asp-Glu-Arg-Glu-Ile-Ser-Val-Pro-Ala-Glu-Ile-Leu-Arg-Lys-Ser-Arg-Arg-Phe-Ala, (SEQ ID NO:16).

2. A peptide having the amino acid sequence:
Leu-Arg-Lys-Ser-Arg-Arg-Phe-Ala-Gln-Ala-Leu-Pro-Val-Trp-Ala-Arg-Pro-Asp-Tyr-Asn, (SEQ ID NO:17).

3. A peptide having the amino acid sequence:
(XVII) Val-Trp-Ala-Arg-Pro-Asp-Tyr-Asn-Pro-Pro-Leu-Val-Glu-Thr-Trp-Lys-Pro-Asp-Tyr, (SEQ ID NO:18).

4. A peptide having the amino acid sequence:
(XVIII) Glu-Thr-Trp-Lys-Lys-Pro-Asp-Tyr-Glu-Pro-Pro-Val-Val-His-Gly-Cys-Pro-Leu-Pro-Pro, (SEQ ID NO:19).

5. A peptide having the amino acid sequence:
(XIX) Val-His-Gly-Cys-Pro-Leu-Pro-Pro-Pro-Lys-Ser-Pro-Pro-Val-Pro-Pro-Pro-Arg-Lys-Lys, (SEQ ID NO:20).

6. A peptide according to any of claims 1–5 wherein said peptide is cyclic.

7. A peptide composition comprising a peptide of any one of claims 1–5 and at least one additional peptide selected from the group consisting of:

(I) Met-Ser-Thr-Ile-Pro-Lys-Pro-Gln-Arg-Lys-Thr-Lys-Arg-Asn-Thr-Asn-Arg-Arg-Pro-Gln, (SEQ ID NO:1)

(II) Pro-Gln-Arg-Lys-Thr-Lys-Arg-Asn-Thr-Asn-Arg-Arg-Pro-Gln-Asp-Val-Lys-Phe-Pro-Gly, (SEQ ID NO:2)

(III) Arg-Asn-Thr-Asn-Arg-Arg-Pro-Gln-Asp-Val-Lys-Phe-Pro-Gly-Gly-Gly-Gln-Ile-Val-Gly, (SEQ ID NO:4)

(IV) Leu-Pro-Arg-Arg-Gly-Pro-Arg-Leu-Gly-Val-Arg-Ala-Thr-Arg-Lys-Thr-Ser-Glu-Arg-Ser, (SEQ ID NO:5)

(V) Thr-Arg-Lys-Thr-Ser-Glu-Arg-Ser-Gln-Pro-Arg-Gly-Arg-Arg-Gln-Pro-Ile-Pro-Lys-Val, (SEQ ID NO:6)

(VI) Arg-Arg-Gln-Pro-Ile-Pro-Lys-Val-Arg-Arg-Pro-Glu-Gly-Arg-Thr-Trp-Ala-Gln-Pro-Gly, (SEQ ID NO:7)

(VII) Gly-Arg-Thr-Trp-Ala-Gln-Pro-Gly-Tyr-Pro-Trp-Pro-Leu-Tyr-Gly-Asn-Glu-Gly-Cys-Gly, (SEQ ID NO:8)

(VIII) Leu-Ser-Gly-Lys-Pro-Ala-Ile-Ile-Pro-Asp-Arg-Glu-Val-Leu-Tyr-Arg-Glu-Phe-Asp-Glu, (SEQ ID NO:9)

(IX) Ile-Ile-Pro-Asp-Arg-Glu-Val-Leu-Tyr-Arg-Glu-Phe-Asp-Glu-Met-Glu-Glu-Cys-Ser-Gln, (SEQ ID NO:10)

(X) Asp-Glu-Met-Glu-Glu-Cys-Ser-Gln-His-Leu-Pro-Tyr-Ile-Glu-Gln-Gly-Met-Met-Leu-Ala, (SEQ ID NO:11)

(XI) Ser-Gln-His-Leu-Pro-Tyr-Ile-Glu-Gln-Gly-Met-Met-Leu-Ala-Glu-Gln-Phe-Lys-Gln-Lys, (SEQ ID NO:12)

(XII) Ile-Glu-Gln-Gly-Met-Met-Leu-Ala-Glu-Gln-Phe-Lys-Gln-Lys-Ala-Leu-Gly-Leu-Leu-Gln, (SEQ ID NO:13)

(XIII) Leu-Ala-Glu-Gln-Phe-Lys-Gln-Lys-Ala-Leu-Gly-Leu-Leu-Gln-Thr-Ala-Ser-Arg-Gln-Ala, (SEQ ID NO:14), and (XIV) Gln-Lys-Ala-Leu-Gly-Leu-Leu-Gln-Thr-Ala-Ser-Arg-Gln-Ala-Glu-Val-Ile-Ala-Pro-Ala, (SEQ ID NO:15).

8. A peptide composition, or peptide according to claim 7 wherein at least one of said peptide is coupled N-terminally, C-terminally or internally to a carrier molecule.

9. A peptide composition, or peptide according to claim 7 wherein at least one of said peptide contains a detectable label.

10. A peptide composition, or peptide according to claim 7 wherein each peptide has on its amino terminus an H, or one or more chemical linking groups, and has on its carboxy terminus an $NH_2$, OH or one or more chemical linking groups.

11. A method for the detection of antibodies to hepatitis C virus present in a body fluid comprising the steps of:
(a) contacting a body fluid of a person to be diagnosed with a peptide composition, or peptide according to claim 7, and,
(b) detecting an immunological complex formed between antibodies in said body fluid and said peptide composition, or peptide as an indication of the presence of antibodies to hepatitis C virus.

12. A kit for the detection of anti-hepatitis C virus antibodies in a body fluid, comprising:
a peptide composition, or peptide according to claim 7, and
a means for detecting an immunological complex formed between said peptide composition, or peptide and said antibodies.

13. A peptide selected from the group consisting of:
(a) a peptide consisting of a combination of at least two of amino acid sequences: SEQ ID NOS:2, 4, 6, 10 and 19,
(b) a peptide consisting of a combination of at least two of amino acid sequences: SEQ ID NOS:1, 2, 6, 10, 12, 17 and 19,
(c) a peptide consisting of a combination of at least two of amino acid sequences: SEQ ID NOS:2, 4, 5, 6, 9, 12, 17 and 19,
(d) a peptide consisting of a combination of at least two of amino acid sequences: SEQ ID NOS:2, 10 and 19,
(e) a peptide consisting of a combination of at least two of amino acid sequences: SEQ ID NOS:2, 4, 5 and 6,
(f) a peptide consisting of a combination of at least two of amino acid sequences: SEQ ID NOS:9, 10, 12, 14 and 15, and
(g) a peptide consisting of a combination of at least two of amino acid sequences: SEQ ID NOS:16, 17, 18, 19 and 20.

14. A peptide composition, or peptide according to any one of claims 1–5 and 13 wherein at least one of said peptide is coupled N-terminally, C-terminally or internally to a carrier molecule.

15. A peptide composition comprising a peptide according to any one of claims 1–5 and 13 wherein at least one peptide contains a detectable label.

16. A peptide composition, or peptide as in any of claims 1–5 and 13 wherein each peptide has on its amino terminus an H, or one or more chemical linking groups, and has on its carboxy terminus an $NH_2$, OH or one or more chemical linking groups.

17. A method for the detection of antibodies to hepatitis C virus present in a body fluid comprising the steps of:

(a) contacting a body fluid of a person to be diagnosed with a peptide composition, or peptide according to any one of claims 1–5 and 13, and, (b) detecting an immunological complex formed between antibodies in said body fluid and said peptide composition, or peptide as an indication of the presence of antibodies to hepatitis C virus.

18. The method of claim 17 wherein said peptide composition, or peptide is present as lines on a nylon membrane.

19. The method of claim 18 wherein said nylon membrane is cut into strips perpendicular to the direction of the peptide composition, or peptide lines, and each strip is incubated with a diluted serum sample.

20. The method of claim 17 wherein said peptide composition, or peptide is present in wells of microtiter plates.

21. A kit for the detection of anti-hepatitis C virus antibodies in a body fluid, comprising:

a peptide composition, or peptide according to any one of claims 1–5 and 13, and a means for detecting an immunological complex formed between said peptide composition, or peptide and said antibodies.

22. The kit of claim 21 further comprising a nylon membrane, said peptide composition, or peptide being present as lines on said membrane, said membrane being cut into strips perpendicular to the direction of the peptide lines, such that each strip can be incubated with a diluted serum sample.

23. The kit of claim 21 further comprising a microtiter plate, said peptide composition being present in the wells of said microtiter plate.

24. A peptide consisting of a combination of at least two peptides selected from the group consisting of:

(XV) Glu-Asp-Glu-Arg-Glu-Ile-Ser-Val-Pro-Ala-Glu-Ile-Leu-Arg-Lys-Ser-Arg-Arg-Phe-Ala, (SEQ ID NO:16)

(XVI) Leu-Arg-Lys-Ser-Arg-Arg-Phe-Ala-Gln-Ala-Leu-Pro-Val-Trp-Ala-Arg-Pro-Asp-Tyr-Asn, (SEQ ID NO:17)

(XVII) Val-Trp-Ala-Arg-Pro-Asp-Tyr-Asn-Pro-Pro-Leu-Val-Glu-Thr-Trp-Lys-Lys-Pro-Asp-Tyr, (SEQ ID NO:18)

(XVIII) Glu-Thr-Trp-Lys-Lys-Pro-Asp-Tyr-Glu-Pro-Pro-Val-Val-His-Gly-Cys-Pro-Leu-Pro-Pro, (SEQ ID NO:19), and (XIX) Val-His-Gly-Cys-Pro-Leu-Pro-Pro-Pro-Lys-Ser-Pro-Pro-Val-Pro-Pro-Pro-Arg-Lys-Lys, (SEQ ID NO:20).

* * * * *